(12) United States Patent
Lee

(10) Patent No.: US 11,447,562 B2
(45) Date of Patent: Sep. 20, 2022

(54) RP215 CHIMERIC ANTIGEN RECEPTOR CONSTRUCT AND METHODS OF MAKING AND USING SAME

(71) Applicant: Chi-Yu Gregory Lee, Vancouver (CA)

(72) Inventor: Chi-Yu Gregory Lee, Vancouver (CA)

(73) Assignee: Chi-Yu Gregory Lee, Vancouver (CA)

( * ) Notice: Subject to any disclaimer, the term of this patent is extended or adjusted under 35 U.S.C. 154(b) by 677 days.

(21) Appl. No.: 16/474,934

(22) PCT Filed: Dec. 22, 2017

(86) PCT No.: PCT/CA2017/051600
§ 371 (c)(1),
(2) Date: Jun. 28, 2019

(87) PCT Pub. No.: WO2018/119518
PCT Pub. Date: Jul. 5, 2018

(65) Prior Publication Data
US 2019/0345257 A1    Nov. 14, 2019

Related U.S. Application Data

(60) Provisional application No. 62/480,207, filed on Mar. 31, 2017, provisional application No. 62/441,382, filed on Jan. 1, 2017.

(51) Int. Cl.
| | | |
|---|---|---|
| *C07K 16/30* | (2006.01) | |
| *C07K 14/55* | (2006.01) | |
| *C07K 14/725* | (2006.01) | |
| *C07K 14/705* | (2006.01) | |
| *C12N 5/0783* | (2010.01) | |
| *C12N 15/86* | (2006.01) | |

(52) U.S. Cl.
CPC ............ *C07K 16/30* (2013.01); *C07K 14/55* (2013.01); *C07K 14/7051* (2013.01); *C07K 14/70517* (2013.01); *C07K 14/70578* (2013.01); *C12N 5/0638* (2013.01); *C12N 15/86* (2013.01); *C07K 2317/622* (2013.01); *C07K 2319/02* (2013.01); *C07K 2319/03* (2013.01); *C12N 2740/16043* (2013.01)

(58) Field of Classification Search
None
See application file for complete search history.

(56) References Cited

U.S. PATENT DOCUMENTS

| | | |
|---|---|---|
| 8,143,373 B2 | 3/2012 | Lee |
| 8,916,371 B2 | 12/2014 | June et al. |
| 8,916,381 B1 | 12/2014 | June et al. |
| 8,974,786 B2 | 3/2015 | Lee |
| 9,273,138 B2 | 3/2016 | Lee |
| 2016/0130356 A1* | 5/2016 | DeSander ............ A61K 47/02 424/183.1 |
| 2017/0291953 A1* | 10/2017 | Tamada .......... C07K 14/70517 |
| 2017/0306046 A1* | 10/2017 | daSilva ............. A61K 47/6851 |
| 2018/0280504 A1* | 10/2018 | da Silva ................ C07K 16/44 |
| 2019/0099446 A1 | 4/2019 | Tamada et al. |
| 2019/0276541 A1* | 9/2019 | Eavarone ............... C07K 16/30 |
| 2019/0322754 A1 | 10/2019 | Lee |
| 2020/0247902 A1* | 8/2020 | Prendergast ..... G01N 33/57492 |

FOREIGN PATENT DOCUMENTS

CN            102775500 A    11/2012

OTHER PUBLICATIONS

Lee, American Journal of Immunology, 2012, 8 (4), 101-116. (Year: 2012).*
Lee, Advances in Bioscience and Biotechnology, 2013, 4, 18-23. (Year: 2013).*
Gregory Lee, Int J Cancer Res Ther, Oct. 25, 2016. "RP215-based Anti-Cancer Drugs," pp. 1-8. (Year: 2016).*
Brentjens et al. Molecular Therapy: Treatment of Chronic Lymphocytic Leukemia with Genetically Targeted Autologous T Cells: Case Report of an Unforeseen Adverse Event in a Phase 1 Clinical Trial. 18 vol. Elsevier, Apr. 1, 2010.
Barczak et al., Mol. Biotechnol., 2015, 57:195-200.
Tang et al., Third-generation CD28/4-BB chimeric antigen receptor T cells for chemotherapy relapsed or refractory acute lymphoblastic leukaemia: a non-randomised, open-label phase I trial protocol. BMJ, 2016, vol. 6, pp. 1-7, ISSN: 2044-6055.
Simmons et al., Use of recombinant lentivirus pseudotyped with vesicular stomatitis virus glycoprotein G for efficient generation of human anti-cancer chimeric T cells by transduction of human peripheral blood lymphocytes in vitro. Virology Journal 2006, 3:8, pp. 1-10, ISSN: 1743-422X.
Lee et al., CA215 and GnRH receptor as targets for cancer therapy Cancer Immunol Immunother (2012) 61:1805-1817, ISSN: 1432-0851.
Liechtenstein et al., Lentiviral Vectors for Cancer Immunotherapy and Clinical Applications. Cancers 2013, 5, 815-837; doi:10.3390/cancers5030815.
U.S. Appl. No. 17/589,474, filed Jan. 31, 2022 by LEE, Chi-Yu Gregory, not yet published.

\* cited by examiner

*Primary Examiner* — Zachary S Skelding
(74) *Attorney, Agent, or Firm* — Oyen Wiggs Green & Mutala LLP

(57) ABSTRACT

A chimeric antigen receptor (CAR) having an antigen binding domain capable of binding to CA215. The antigen binding domain can have a binding affinity and specificity similar to the RP215 antibody. Methods of making and using such CARs are provided. The CARs can be used to treat cancer.

6 Claims, 20 Drawing Sheets
Specification includes a Sequence Listing.

Amino Acid Sequence of Humanized IgG1 Heavy Chain for RP215:
MDPKGSLSWRILLFLSLAFELSYGQVQLVQSGAEVKKPGASVKVSCKASGYTFTDYWMHWVRQ
APGQGLEWMGAIDTSDSYTRYAQKFQGRVTMTVDESTSTVYMELSSLRSEDTAVYYCARSIYD
WGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGN
VFSCSVMHEALHNHYTQKSLSLSPG*
(SEQ ID NO.:1)

*Underlined above is the heavy chain constant region sequence.*

FIG. 1A

Nucleic Acid Sequence of Humanized IgG1 Heavy Chain for RP215:
ATGGACCCCAAGGGCAGCCTGAGCTGGAGAATCCTGCTGTTCCTGAGCCTGGCCTTCGAGCTGAGC
TACGGCCAGGTGCAGCTTGTTCAGAGTGGCGCCGAAGTGAAGAAGCCAGGCGCTTCCGTGAAGGTG
AGCTGCAAGGCATCAGGCTACACCTTCACTGATTATTGGATGCACTGGGTGAGACAGGCACCCGGT
CAGGGGCTCGAATGGATGGGCGCCATCGATACTAGCGATTCCTATACCAGATACGCACAGAAGTTT
CAGGGAAGAGTTACCATGACTGTCGATGAATCTACAAGCACCGTCTACATGGAGCTGAGCAGCCTG
CGGTCTGAGGACACCGCTGTTTACTACTGTGCCCGCTCCATCTATGATTGGGGTCAAGGAACCTTG
GTCACAGTGAGTTCTGCTAGCACCAAGGGCCCCAGCGTGTTCCCTCTGGCCCCCAGCAGCAAGAGC
ACCAGCGGCGGAACCGCCGCCCTGGGCTGCCTGGTGAAGGACTACTTCCCCGAGCCCGTGACCGTG
TCCTGGAACAGCGGCGCTCTGACCAGCGGAGTGCACACCTTCCCTGCCGTGCTGCAGAGCAGCGGC
CTGTACTCCCTGAGCAGCGTGGTGACCGTGCCCAGCAGCAGCCTGGGCACCCAGACCTACATCTGC
AACGTGAACCACAAGCCCTCCAACACCAAGGTGGACAAGAAGGTGGAGCCTAAGAGCTGCGACAAG
ACCCACACCTGCCCTCCCTGCCCCGCCCCGAGCTGCTGGGCGGACCCAGCGTGTTCCTGTTCCCT
CCCAAGCCCAAGGACACCCTGATGATCAGCCGCACCCCCGAGGTGACCTGCGTGGTGGTGGACGTG
AGCCACGAGGACCCCGAGGTGAAGTTCAACTGGTACGTGGACGGCGTGGAGGTGCACAACGCCAAG
ACCAAGCCTCGGGAGGAGCAGTACAACTCCACCTACCGCGTGGTGAGCGTGCTGACCGTGCTGCAC
CAGGACTGGCTGAACGGCAAGGAGTACAAGTGCAAGGTGAGCAACAAGGCCCTGCCCGCTCCCATC
GAGAAGACCATCAGCAAGGCCAAGGGCCAGCCCCGGGAGCCTCAGGTGTACACCCTGCCCCCCAGC
CGCGACGAGCTGACCAAGAACCAGGTGAGCCTGACCTGCCTGGTGAAGGGCTTCTACCCCTCCGAC
ATCGCCGTGGAGTGGGAGAGCAACGGCCAGCCTGAGAACAACTACAAGACCACCCCTCCCGTGCTG
GACAGCGACGGCAGCTTCTTCCTGTACAGCAAGCTGACCGTGGACAAGTCCCGGTGGCAGCAGGGC
AACGTGTTCAGCTGCAGCGTGATGCACGAGGCCCTGCACAACCACTACACCCAGAAGAGCCTGAGC
CTGAGCCCCGGATAG
(SEQ ID NO.:2)

FIG. 1B

Amino Acid Sequence of Kappa Light Chain for Humanized RP215:
METDTLLLWVLLLWVPGSTGDIVMTQSPDSLAVSLGERATINCKSSQSLLNSSNQKSYLAWYQQ
KPGQPPKLLVYFASTRESGVPDRFSGSGSGTDFTLTISSLQAEDVAVYFCQQHYSTPSTFGGGT
KLEIK<u>RTVAAPSVFIFPPSDEQLKSGTASVVCLLNNFYPREAKVQWKVDNALQSGNSQESVTEQ</u>
<u>DSKDSTYSLSSTLTLSKADYEKHKVYACEVTHQGLSSPVTKSFNRGEC</u>*
(SEQ ID NO.:3)

*Underlined above is the light chain constant region sequence.*

FIG. 1C

Nucleic Acid Sequence of Kappa Light Chain for Humanized RP215:
ATGGAGACCGACACCCTGCTGCTCTGGGTGCTGCTGCTCTGGGTGCCCGGCTCCACCGGAGATA
TCGTGATGACCCAGTCCCCCGACAGCCTGGCCGTCTCTCTGGGTGAGCGGGCAACCATCAACTG
TAAGTCTAGCCAGTCCCTGTTGAACAGTAGCAATCAAAAGAGCTATCTTGCCTGGTATCAG
CAAAAGCCTGGCCAGCCACCAAAACTGCTTGTCTATTTCGCTTCCACTCGGGAAAGCGGTG
TACCAGACCGCTTTTCTGGCTCAGGTTCCGGCACAGACTTTACCTTGACCATTAGCTCCCT
TCAGGCAGAGGACGTGGCAGTCTACTTTTGCCAGCAACACTACTCCACTCCATCAACCTTT
GGAGGTGGCACAAAACTGGAGATTAAGCGGACCGTGGCCGCCCCAGCGTGTTCATCTTCC
CTCCCAGCGACGAGCAGCTGAAGTCTGGCACCGCCAGCGTGGTGTGCCTGCTGAACAACTT
CTACCCCCGCGAGGCCAAGGTGCAGTGGAAGGTGGACAACGCCCTGCAGAGCGGCAACAGC
CAGGAGAGCGTGACCGAGCAGGACTCCAAGGACAGCACCTACAGCCTGAGCAGCACCCTGA
CCCTGAGCAAGGCCGACTACGAGAAGCACAAGGTGTACGCCTGCGAGGTGACCCACCAGGG
ACTGTCTAGCCCCGTGACCAAGAGCTTCAACCGGGGCGAGTGCTAA
(SEQ ID NO.:4)

FIG. 1D

Amino Acid Sequence of Humanized RP215 Heavy Chain:
QVQLVQSGAEVKKPGASVKVSCKASGYTFTDYWMHWVRQAPGQGLEWMGAIDTSDSYTRYA
QKFQGRVTMTVDESTSTVYMELSSLRSEDTAVYYCARSIYDWGQGTLVTVSS
(SEQ ID NO.:5)

FIG. 2B

Amino Acid Sequence of Humanized RP215 Light Chain:
DIVMTQSPDSLAVSLGERATINCKSSQSLLNSSNQKSYLAWYQQKPGQPPKLLVYFASTRE
SGVPDRFSGSGSGTDFTLTISSLQAEDVAVYFCQQHYSTPSTFGGGTKLEIK
(SEQ ID NO.:6)

FIG. 2C

Amino Acid Sequence of RP215 Cytokine Fusion Protein (SEQ ID NO:7)

[Signal Peptide] AATMALPVTALLLPLALLLHAARP

[hRP215scFv] QVQLVQSGAEVKKPGASVKVSCKASGYTFTDYWMHWVRQAPGQGLEWM
GAIDTSDSYTRYAQKFQGRVTMTVDESTSTVYMELSSLRSEDTAVYYCARSIYDWGQGTLV
TVSSGGGGSGGGGSGGGGSDIVMTQSPDSLAVSLGERATINCKSSQSLLNSSNQKSYLAWY
QQKPGQPPKLLVYFASTRESGVPDRFSGSGSGTDFTLTISSLQAEDVAVYFCQQHYSTPST
FGGGTKLEIK

[CD8] TTTPAPRPPTPAPTIASQPLSLRPEACRPAAGGAVHTRGLDFACDIYIWAPLAG
TCGVLLLSLVITLYC

[4-1BB] KRGRKKLLYIFKQPFMRPVQTTQEEDGCSCRFPEEEEGGCE

[CD3Z] LRVKFSRSADAPAYKQGQNQLYNELNLGRREEYDVLDKRRGRDPEMGGKPRRKNP
QEGLYNELQKDKMAEAYSEIGMKGERRRGKGHDGLYQGLSTATKDTYDALHMQALPPR

[2A] EGRGSLLTCGDVEENPGP

[IL7] MFHVSFRYIFGLPPLILVLLPVASSDCDIEGKDGKQYESVLMVSIDQLLDSMKE
IGSNCLNNEFNFFKRHICDANKEGMFLFRAARKLRQFLKMNSTGDFDLHLLKVSEGTTI
LLNCTGQVKGRKPAALGEAQPTKSLEENKSLKEQKKLNDLCFLKRLLQEIKTCWNKILMG
TKEH

FIG. 2D

SEQUENCE LISTING

```
<160> NUMBER OF SEQ ID NOS: 16

<210> SEQ ID NO 1
<211> LENGTH: 466
<212> TYPE: PRT
<213> ORGANISM: Artificial Sequence
<220> FEATURE:
<223> OTHER INFORMATION: Synthetic Construct

<400> SEQUENCE: 1

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Asp Tyr Trp Met His Trp Val Arg Gln Ala
    50                  55                  60

Pro Gly Gln Gly Leu Glu Trp Met Gly Ala Ile Asp Thr Ser Asp Ser
65                  70                  75                  80

Tyr Thr Arg Tyr Ala Gln Lys Phe Gln Gly Arg Val Thr Met Thr Val
                85                  90                  95

Asp Glu Ser Thr Ser Thr Val Tyr Met Glu Leu Ser Ser Leu Arg Ser
            100                 105                 110

Glu Asp Thr Ala Val Tyr Tyr Cys Ala Arg Ser Ile Tyr Asp Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
```

|  |  |  | 260 |  |  |  | 265 |  |  |  | 270 |  |
|--|--|--|--|--|--|--|--|--|--|--|--|--|

Ile Ser Arg Thr Pro Glu Val Thr Cys Val Val Asp Val Ser His
            275                 280                 285
Glu Asp Pro Glu Val Lys Phe Asn Trp Tyr Val Asp Gly Val Glu Val
        290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly
465

<210> SEQ ID NO 2
<211> LENGTH: 1401
<212> TYPE: DNA
<213> ORGANISM: Artificial Sequence
<220> FEATURE:
<223> OTHER INFORMATION: Synthetic Construct

<400> SEQUENCE: 2

```
atggacccca agggcagcct gagctggaga atcctgctgt tcctgagcct ggccttcgag      60
ctgagctacg ccaggtgca gcttgttcag agtggcgccg aagtgaagaa gccaggcgct     120
tccgtgaagg tgagctgcaa ggcatcaggc tacaccttca ctgattattg gatgcactgg     180
gtgagacagg cacccggtca ggggctcgaa tggatgggcg ccatcgatac tagcgattcc     240
tataccagat acgcacagaa gtttcaggga gagttacca tgactgtcga tgaatctaca     300
agcaccgtct acatggagct gagcagcctg cggtctgagg acaccgctgt ttactactgt     360
gcccgctcca tctatgattg ggtcaagga accttggtca cagtgagttc tgctagcacc     420
aagggcccca gcgtgttccc tctggccccc agcagcaaga gcaccagcgg cggaaccgcc     480
gccctgggct gcctggtgaa ggactacttc cccgagcccg tgaccgtgtc ctggaacagc     540
ggcgctctga ccagcggagt gcacaccttc cctgccgtgc tgcagagcag cggcctgtac     600
tccctgagca gcgtggtgac cgtgcccagc agcagcctgg gcacccagac ctacatctgc     660
aacgtgaacc acaagccctc caacaccaag gtggacaaga aggtggagcc taagagctgc     720
gacaagaccc acacctgccc tcctgccccc gccccgagc tgctgggcgg acccagcgtg     780
ttcctgttcc ctcccaagcc caaggacacc ctgatgatca gccgcacccc cgaggtgacc     840
```

```
tgcgtggtgg tggacgtgag ccacgaggac cccgaggtga agttcaactg gtacgtggac      900
ggcgtggagg tgcacaacgc caagaccaag cctcgggagg agcagtacaa ctccacctac      960
cgcgtggtga gcgtgctgac cgtgctgcac caggactggc tgaacggcaa ggagtacaag     1020
tgcaaggtga gcaacaaggc cctgcccgct cccatcgaga agaccatcag caaggccaag     1080
ggccagcccc gggagcctca ggtgtacacc ctgccccca gccgcgacga gctgaccaag      1140
aaccaggtga gcctgacctg cctggtgaag ggcttctacc cctccgacat cgccgtggag     1200
tgggagagca acggccagcc tgagaacaac tacaagacca cccctcccgt gctggacagc     1260
gacggcagct tcttcctgta cagcaagctg accgtggaca gtccggtg gcagcagggc      1320 aacgtgttca gctgcagcgt gatgcacgag gccctgcaca accactacac ccagaagagc     1380
ctgagcctga gccccggata g                                               1401
```

<210> SEQ ID NO 3
<211> LENGTH: 240
<212> TYPE: PRT
<213> ORGANISM: Artificial Sequence
<220> FEATURE:
<223> OTHER INFORMATION: Synthetic Construct

<400> SEQUENCE: 3

```
Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Asn Ser Ser Asn Gln Lys Ser Tyr Leu Ala Trp Tyr Gln Gln
    50                  55                  60

Lys Pro Gly Gln Pro Pro Lys Leu Leu Val Tyr Phe Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Phe Cys Gln Gln His Tyr Ser Thr Pro Ser Thr Phe Gly Gly Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 4
<211> LENGTH: 723
<212> TYPE: DNA

<213> ORGANISM: Artificial Sequence
<220> FEATURE:
<223> OTHER INFORMATION: Synthetic Construct

<400> SEQUENCE: 4

```
atggagaccg acaccctgct gctctgggtg ctgctgctct gggtgcccgg ctccaccgga    60
gatatcgtga tgacccagtc ccccgacagc ctggccgtct ctctgggtga gcgggcaacc   120
atcaactgta gtctagcca gtccctgttg aacagtagca atcaaaagag ctatcttgcc   180
tggtatcagc aaaagcctgg ccagccacca aaactgcttg tctatttcgc ttccactcgg   240
gaaagcggtg taccagaccg cttttctggc tcaggttccg gcacagactt taccttgacc   300
attagctccc ttcaggcaga ggacgtggca gtctactttt gccagcaaca ctactccact   360
ccatcaacct ttggaggtgg cacaaaactg gagattaagc ggaccgtggc cgcccccagc   420
gtgttcatct ccctcccag cgacgagcag ctgaagtctg gcaccgccag cgtggtgtgc   480
ctgctgaaca acttctaccc ccgcgaggcc aaggtgcagt ggaaggtgga caacgccctg   540
cagagcggca cagccagga gagcgtgacc gagcaggact ccaaggacag cacctacagc   600
ctgagcagca ccctgaccct gagcaaggcc gactacgaga agcacaaggt gtacgcctgc   660
gaggtgaccc accagggact gtctagcccc gtgaccaaga gcttcaaccg ggcgagtgc   720
taa                                                                 723
```

<210> SEQ ID NO 5
<211> LENGTH: 113
<212> TYPE: PRT
<213> ORGANISM: Artificial Sequence
<220> FEATURE:
<223> OTHER INFORMATION: Synthetic Construct

<400> SEQUENCE: 5

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Ala Ile Asp Thr Ser Asp Ser Tyr Thr Arg Tyr Ala Gln Lys Phe
    50                  55                  60

Gln Gly Arg Val Thr Met Thr Val Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Trp Gly Gln Gly Thr Leu Val Thr Val Ser
            100                 105                 110

Ser
```

<210> SEQ ID NO 6
<211> LENGTH: 113
<212> TYPE: PRT
<213> ORGANISM: Artificial Sequence
<220> FEATURE:
<223> OTHER INFORMATION: Synthetic Construct

<400> SEQUENCE: 6

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
```

```
                20                  25                  30
Ser Asn Gln Lys Ser Tyr Leu Ala Trp Tyr Gln Gln Lys Pro Gly Gln
            35                  40                  45

Pro Pro Lys Leu Leu Val Tyr Phe Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Ser Thr Pro Ser Thr Phe Gly Gly Gly Thr Lys Leu Glu Ile
            100                 105                 110

Lys

<210> SEQ ID NO 7
<211> LENGTH: 683
<212> TYPE: PRT
<213> ORGANISM: Artificial Sequence
<220> FEATURE:
<223> OTHER INFORMATION: Synthetic Construct

<400> SEQUENCE: 7

Ala Ala Thr Met Ala Leu Pro Val Thr Ala Leu Leu Leu Pro Leu Ala
1               5                   10                  15

Leu Leu Leu His Ala Ala Arg Pro Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Asp Tyr Trp Met His Trp Val Arg Gln Ala
    50                  55                  60

Pro Gly Gln Gly Leu Glu Trp Met Gly Ala Ile Asp Thr Ser Asp Ser
65                  70                  75                  80

Tyr Thr Arg Tyr Ala Gln Lys Phe Gln Gly Arg Val Thr Met Thr Val
                85                  90                  95

Asp Glu Ser Thr Ser Thr Val Tyr Met Glu Leu Ser Ser Leu Arg Ser
            100                 105                 110

Glu Asp Thr Ala Val Tyr Tyr Cys Ala Arg Ser Ile Tyr Asp Trp Gly
        115                 120                 125

Gln Gly Thr Leu Val Thr Val Ser Ser Gly Gly Gly Ser Gly Gly
    130                 135                 140

Gly Gly Ser Gly Gly Gly Ser Asp Ile Val Met Thr Gln Ser Pro
145                 150                 155                 160

Asp Ser Leu Ala Val Ser Leu Gly Glu Arg Ala Thr Ile Asn Cys Lys
            165                 170                 175

Ser Ser Gln Ser Leu Leu Asn Ser Asn Gln Lys Ser Tyr Leu Ala
        180                 185                 190

Trp Tyr Gln Gln Lys Pro Gly Gln Pro Pro Lys Leu Leu Val Tyr Phe
    195                 200                 205

Ala Ser Thr Arg Glu Ser Gly Val Pro Asp Arg Phe Ser Gly Ser Gly
    210                 215                 220

Ser Gly Thr Asp Phe Thr Leu Thr Ile Ser Ser Leu Gln Ala Glu Asp
225                 230                 235                 240

Val Ala Val Tyr Phe Cys Gln Gln His Tyr Ser Thr Pro Ser Thr Phe
                245                 250                 255

Gly Gly Gly Thr Lys Leu Glu Ile Lys Thr Thr Thr Pro Ala Pro Arg
            260                 265                 270
```

```
Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
        290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
                355                 360                 365

Glu Glu Glu Gly Gly Cys Glu Leu Arg Val Lys Phe Ser Arg Ser Ala
        370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
        450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Glu Gly Arg Gly Ser Leu Leu Thr
                485                 490                 495

Cys Gly Asp Val Glu Glu Asn Pro Gly Pro Met Phe His Val Ser Phe
                500                 505                 510

Arg Tyr Ile Phe Gly Leu Pro Pro Leu Ile Leu Val Leu Leu Pro Val
        515                 520                 525

Ala Ser Ser Asp Cys Asp Ile Glu Gly Lys Asp Gly Lys Gln Tyr Glu
        530                 535                 540

Ser Val Leu Met Val Ser Ile Asp Gln Leu Leu Asp Ser Met Lys Glu
545                 550                 555                 560

Ile Gly Ser Asn Cys Leu Asn Asn Glu Phe Asn Phe Lys Arg His
                565                 570                 575

Ile Cys Asp Ala Asn Lys Glu Gly Met Phe Leu Phe Arg Ala Ala Arg
                580                 585                 590

Lys Leu Arg Gln Phe Leu Lys Met Asn Ser Thr Gly Asp Phe Asp Leu
                595                 600                 605

His Leu Leu Lys Val Ser Glu Gly Thr Thr Ile Leu Leu Asn Cys Thr
        610                 615                 620

Gly Gln Val Lys Gly Arg Lys Pro Ala Ala Leu Gly Glu Ala Gln Pro
625                 630                 635                 640

Thr Lys Ser Leu Glu Glu Asn Lys Ser Leu Lys Glu Gln Lys Lys Leu
                645                 650                 655

Asn Asp Leu Cys Phe Leu Lys Arg Leu Leu Gln Glu Ile Lys Thr Cys
                660                 665                 670

Trp Asn Lys Ile Leu Met Gly Thr Lys Glu His
                675                 680
```

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggcactgaca attccgtggt                                               20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
agggacgtag cagaaggacg                                               20

<210> SEQ ID NO 10
<211> LENGTH: 23
<212> TYPE: DNA
<213> ORGANISM: Artificial Sequence
<220> FEATURE:
<223> OTHER INFORMATION: Probe

<400> SEQUENCE: 10
acgtcctttc catggctgct cgc                                           23

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gctgtcatct cttgtgggct gt                                            22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
actcatggga gctgctggtt c                                             21

<210> SEQ ID NO 13
<211> LENGTH: 26
<212> TYPE: DNA
<213> ORGANISM: Artificial Sequence
<220> FEATURE:
<223> OTHER INFORMATION: Probe

<400> SEQUENCE: 13
cctgtcatgc ccacacaaat ctctcc                                        26

<210> SEQ ID NO 14
<211> LENGTH: 20
<212> TYPE: DNA
<213> ORGANISM: Artificial Sequence
<220> FEATURE:
<223> OTHER INFORMATION: Primer

```
<400> SEQUENCE: 14
tgacagccgc ctagcatttc                                               20

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
gctcgatatc agcagttctt gaag                                          24

<210> SEQ ID NO 16
<211> LENGTH: 22
<212> TYPE: DNA
<213> ORGANISM: Artificial Sequence
<220> FEATURE:
<223> OTHER INFORMATION: Probe

<400> SEQUENCE: 16
cacgtggccc gagagctgca tc                                            22
```

RP215 CHIMERIC ANTIGEN RECEPTOR CONSTRUCT AND METHODS OF MAKING AND USING SAME

REFERENCE TO RELATED APPLICATIONS

This application is a national stage entry under 35 U.S.C. § 371 of Patent Cooperation Treaty patent application No. PCT/CA2017/051600, which claims the benefit under 35 U.S.C. § 119 of U.S. provisional patent application No. 62/441,382 filed 1 Jan. 2017 and U.S. provisional patent application No. 62/480,207 filed 31 Mar. 2017. Both of the foregoing applications are incorporated by reference herein for all purposes in their entireties.

TECHNICAL FIELD

Some embodiments of the invention relate to the fields of immunology, cell biology, molecular biology, and medicine, including cancer medicine. Some embodiments of the invention relate to the field of a chimeric antigen receptor (CAR) that targets CA215, nucleotide constructs encoding such a CAR, and methods of making and using same.

BACKGROUND

RP215 is a monoclonal antibody generated in 1987 and later shown to react with a carbohydrate-associated epitope (CA215) found mainly in immunoglobulins expressed by most cancer cells in humans, including those from the ovary, cervix, lung and liver. In contrast, an RP215-specific epitope is not found in normal immunoglobulin produced by B cells. RP215 in either murine or humanized forms has been shown to induce apoptosis and complement-dependent cytotoxicity to almost all cancer cells. Therefore, RP215 has therapeutic potential as a highly specific monoclonal antibody which targets a wide variety of cancers in humans.

U.S. Pat. No. 8,974,786 to Lee, which is incorporated by reference herein in its entirety for all purposes, discloses the nucleotide and amino acid sequence for murine RP215 and humanized RP215. Biochemical and immunological experiments demonstrate that both murine and humanized RP215 have high specificity and affinity to CA215 (mainly cancerous immunoglobulins) on cancer cell surface. It has been documented that both murine and humanized forms of RP215, including scFv fragments thereof, will induce apoptosis of treated cancer cells as well as complement-dependent cytotoxicity and lead to cytotoxic killing of the treated cancer cells.

As disclosed in U.S. Pat. No. 8,974,786 to Lee, humanized RP215 monoclonal antibody has been found to be bioequivalent to murine RP215 at recognizing a carbohydrate-associated epitope in the cancer cell surface expressed CA215. U.S. Pat. No. 8,143,373 to Lee is also of interest with respect to the subject matter described herein, and is incorporated by reference herein in its entirety for all purposes. This patent discloses that the epitope of CA215 shows very intense staining on human cancers of the ovary, cervix, endometrium, colon, stomach, intestine, esophagus, breast, and lung, as well as being present in liver and kidney cancer cell lines as well as lymphoma, melanoma, neuroblastoma, bone, and prostate cancer cell lines.

Chimeric antigen receptors (CARs) are artificial receptors that convey antigen specificity to cells, such as T cells. CAR in T cell therapy (CAR-T) technology combines T cell immunotherapy, gene therapy and immunotherapy. CAR-T has been used for cancer treatments and it involves modifying a patient's T cells. The modified T cells express CARs, which are antigen receptors recognizing cell surface antigens on tumor cells. Upon antigen binding, the modified T cells can initiate an immune response, such as the release of cytokine to induce tumor cell death. Attempts in using CAR-T to treat cancer have met with some success. Successful examples have been reported for CAR-T cell therapy of different types of blood cancers, for example by using a CD19-related CAR platform. U.S. Pat. No. 8,916,381, incorporated by reference herein in its entirety, discloses a method of treating leukemia with CAR-T. Brentjens et al. (Molecular Therapy: Treatment of Chronic Lymphocytic Leukemia with Genetically Targeted Autologous T Cells: Case Report of an Unforeseen Adverse Event in a Phase I Clinical Trial. 18 Vol. Elsevier, Apr. 1, 2010), incorporated by reference herein in its entirety, conducted a clinical trial to treat chronic lymphocytic leukemia with CAR-T. The modified T cells were designed to recognize CA19, which is expressed on most B-cell malignancies.

There remains a need for improved constructs and methods for selectively targeting and killing cancer cells.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a nucleotide vector capable of expressing an RP215 CAR. In some aspects, the RP215 CAR encodes a polypeptide having from N-terminal to C-terminal an antigen binding domain capable of binding to CA215, a hinge domain, a transmembrane domain; and an intracellular T cell signaling domain. In some aspects, the antigen binding domain is an scFv of RP215.

One aspect of the invention provides a polypeptide that is an RP215 CAR that has an antigen binding domain capable of binding to CA215. In some aspects, the polypeptide that is an RP215 CAR has an antigen binding domain capable of binding to CA215, a transmembrane domain, and an intracellular T cell signaling domain. In some aspects, immune cells that express the RP215 CAR are able to selective bind to and kill cells expressing CA215. In some embodiments, the cells expressing CA215 are cancer cells.

One aspect of the invention provides a method of producing an immune cell capable of expressing an RP215 CAR. The method involves isolating the immune cells from the subject and genetically engineering the immune cells to express an RP215 CAR. In some aspects, the genetic engineering can be carried out using a lentiviral vector. In some aspects, the immune cells are introduced into the body of a patient suffering from cancer or another disorder involving a high expression of CA215 to treat the cancer or the disorder.

In addition to the exemplary aspects and embodiments described above, further aspects and embodiments will become apparent by reference to the drawings and by study of the following detailed descriptions.

BRIEF DESCRIPTION OF THE DRAWINGS

In drawings which illustrate non-limiting embodiments of the invention:

FIGS. 1A and 1B show amino acid and nucleotide sequences, respectively of the heavy chain of a humanized RP215 antibody (SEQ ID NOs:1-2). FIGS. 1C-1D show the amino acid and nucleotide sequences, respectively, of the light chain of a humanized RP215 antibody (SEQ ID NOS: 3-4). The sequences of the humanized RP215 antibody were deduced from antibodies produced by a stable cell line, UY463-RP215.

FIGS. 2B and 2C show amino acid sequences of the scFv fragment of the exemplary RP215 CAR nucleotide vector construct shown in FIG. 2A. FIG. 2B shows the amino acid sequence of the $V_H$ domain of the scFv fragment (SEQ ID NO:5). FIG. 2C shows the amino acid sequence of the $V_L$ domain of the scFv fragment (SEQ ID NO:6).

FIG. 2D shows the amino acid sequence of the exemplary RP215 CAR construct shown in FIG. 2A fused with an IL7 cytokine (SEQ ID NO:7). Although the sequences of FIG. 2D have been separated into different sections to illustrate the different domains of the RP215 CAR fusion protein construct, the sequences are one continuous polypeptide.

FIG. 5A shows the WPRE standard curve and FIG. 5B shows the ALB standard curve.

FIG. 6A shows the ALB standard curve and FIG. 6B shows the LTR standard curve. These two standard curves were used to determine the average number of copies of the exemplary RP215 CAR-T nucleotide vector construct in genetically modified T cells.

DESCRIPTION

Figure 2A:
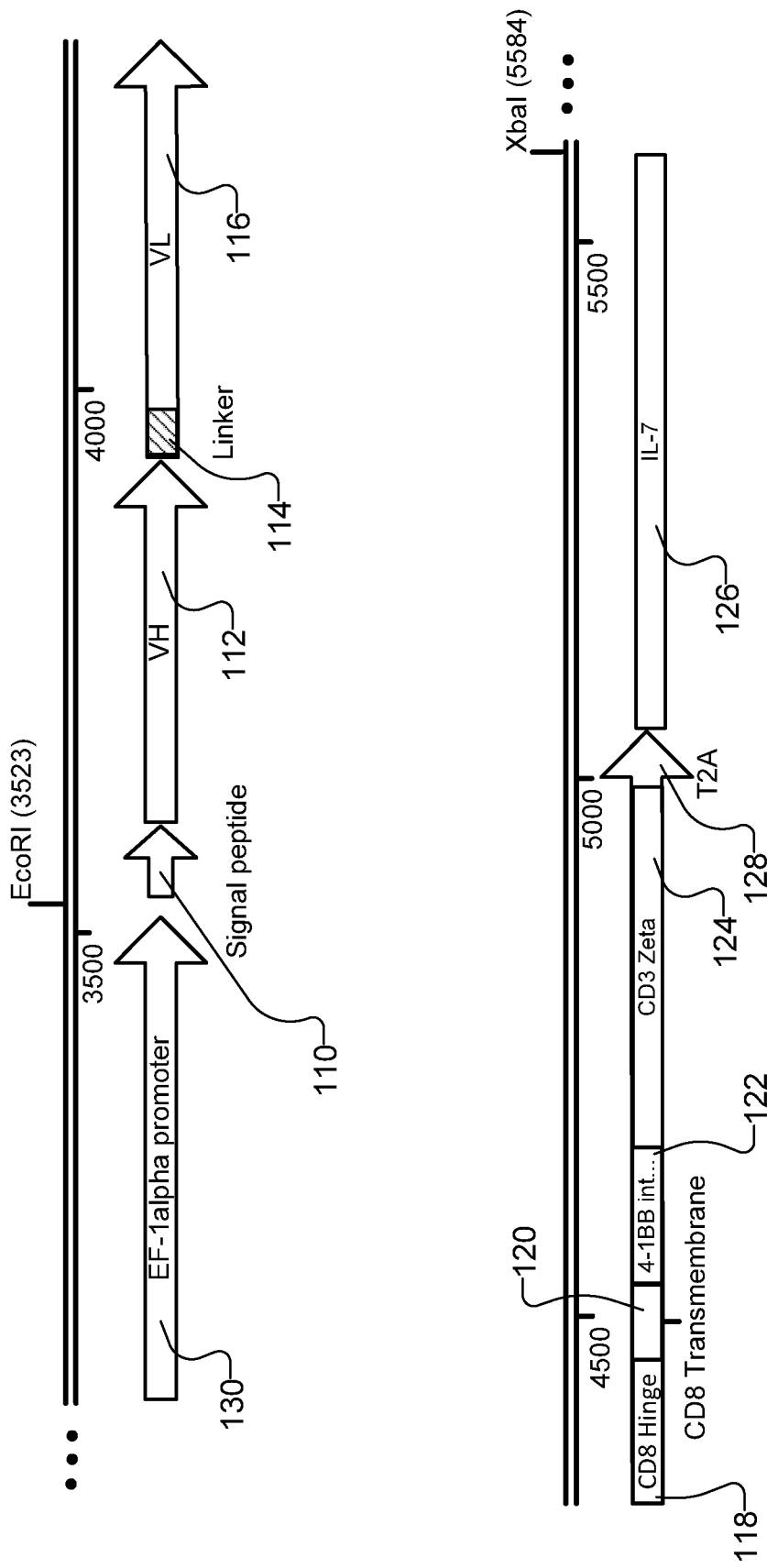
FIG. 2A is a schematic diagram showing the domains of a first example embodiment of a nucleotide vector capable of expressing an RP215 CAR The illustrated embodiment is a CAR lentiviral vector.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The terms "antibody" and "immunoglobulins" refer to antibodies of any isotype and fragments of antibodies that bind specifically to an antigen. Some examples of antibodies include but are not limited to humanized antibodies, chimeric antibodies, and proteins comprising an antigen-binding portion of an antibody.

The term "antibody fragment" refers to a portion of an antibody. Some examples of antibody fragments include but are not limited to an antigen binding (Fab) fragment, an F(ab)$_2$ fragment, an Fab' fragment, or a variable domain (Fv).

The term "single-chain variable fragment" (scFv fragment) refers to a single polypeptide chain, comprising the variable regions of the light ($V_L$) and heavy ($V_H$) chains of an antibody. The $V_L$ and $V_H$ regions are joined by a suitable linker.

The term "affinity" refers to the strength of the binding interaction between a single biomolecule and its ligand or binding partner. In some embodiments, the strength of the binding interaction is measured by the equilibrium constant for the reversible binding of two molecules, which can be expressed as a dissociation constant ($K_d$).

The terms "treat", "treating" and "treatment" refer to an approach for obtaining desired clinical results. Desired clinical results can include, but are not limited to, reduction or alleviation of at least one symptom of a disease. For example, treatment can be diminishment of at least one symptom of disease, diminishment of extent of disease, stabilization of disease state, prevention of spread of disease, delay or slowing of disease progression, palliation of disease, diminishment of disease reoccurrence, remission of disease, prolonging survival with disease, or complete eradication of disease.

The terms "cancer cell" and "tumor cell" refer to cells, the growth and division of which can be typically characterized as unregulated. Cancer cells can be of any origin, including benign and malignant cancers, metastatic and non-metastatic cancers, and primary and secondary cancers.

The term "chimeric antigen receptor (CAR)" refers to an engineered receptor. A typical CAR has an antigen binding domain that binds to a desired target antigen, a transmembrane domain, and an intracytoplasmic domain. The antigen binding domain of a CAR can be provided by the scFv of a monoclonal antibody. The transmembrane domain and the intracytoplasmic domain can be provided by the CD3-zeta transmembrane and ectodomains. A typical CAR will also include a signal peptide at its amino-terminal end, to direct the nascent translated protein into the endoplasmic reticulum so that the antigen binding domain will be presented on the surface of the immune cell in which the CAR is expressed.

In some embodiments, a chimeric antigen receptor (CAR) comprising an antigen-binding fragment of a humanized RP215 monoclonal antibody is provided, and is referred to herein as an RP215 CAR. An RP215 CAR is a CAR that is able to bind to CA215.

In some embodiments, the RP215 CAR comprises the scFv fragment of a humanized RP215 antibody, and can be expressed following introduction of a nucleotide vector encoding the RP215 CAR into suitable immune cells, for example, T cells. In some embodiments, the antigen binding domain of the RP215 CAR binds to CA215. In some embodiments, the RP215 CAR exhibits similar binding affinity and specificity towards CA215 as does a humanized RP215 antibody.

Some embodiments of the invention relate to the field of a lentiviral chimeric antigen receptor (CAR) nucleotide construct including portions of a humanized RP215 gene that provides a nucleotide vector capable of expressing an RP215 CAR in a transduced immune cell. Humanized RP215 is murine RP215 monoclonal antibody in humanized form which recognizes and binds specifically to CA215. CA215 is highly expressed on the surface of cancer cells of many tissue origins.

In some embodiments, upon transduction of a nucleotide vector encoding the RP215 CAR into suitable immune cells, for example, T cells or NK cells isolated from an individual patient, the RP215 CAR-transduced immune cells will then express an RP215 CAR construct with an antigen binding region comprising an scFv chain of a humanized RP215 antibody. This immunoglobulin chain will bind to a carbohydrate-associated epitope in the CA215 expressed on cancer cells and result in cytotoxic killing of the cancer cells. The carbohydrate-associated epitope is expressed on a number of different types of cancer cells, including ovarian, cervical, endometrial, colon, stomach, intestine, esophageal, breast, lung, liver, kidney, bone, and prostate cancers, as well as lymphoma, melanoma and neuroblastoma. Therefore, the RP215 CAR construct can potentially be utilized for therapeutic applications for treatment of cancers including these types of cancer.

Applications of RP215-related CAR-T technology in cancer immunotherapy can be achieved by genetically modifying appropriate immune cells, e.g. T cells, by insertion of a nucleotide vector encoding an RP215 CAR, so that those immune cells will subsequently express an RP215 CAR comprising an scFv of RP215 that can bind to CA215 expressed on the cancer cell surface to induce apoptosis and related cytotoxic killing of tumor cells, in vitro and in vivo.

An RP215 CAR construct can be transduced into isolated immune cells, e.g. T cells, of a given patient. These modified immune cells, e.g. T cells, from the given patient can be expanded by in vitro culture, and then transfused to the same given patient. In some embodiments, the isolated immune cells, e.g. T cells, are obtained from a healthy subject, genetically modified to insert a nucleotide vector capable of expressing an RP215 CAR therein, and then introduced into the bloodstream of a patient suffering from cancer. Cancer immunotherapy using an RP215 CAR can be used in the treatment of cancer, for example for inhibition and/or reduction of tumor growth.

In view of the widespread expression of CA215 on the surface of a large number of different varieties of human cancer cells, it can be expected that the RP215 CAR construct will have broad therapeutic applications to many forms of human cancers which have an associated high level of expression of CA215.

With reference to the figures, a specific example embodiment of an RP215 CAR is now described. In some embodiments, the antigen binding domain of the RP215 CAR comprises a peptide that binds to CA215 in a manner similar to the RP215 antibody. U.S. Pat. No. 8,974,786 to Lee discloses the nucleotide sequence of humanized RP215 antibody. In that reference, the sequence was verified by repeated sequencing and molecular biological analysis. The antibody-producing stable cell line for a humanized RP215 antibody was established and disclosed by that reference.

The amino acid and nucleotide sequences of an example embodiment of a humanized RP215 monoclonal antibody are shown in FIGS. 1A-1D. The heavy chain of the humanized RP215 antibody is encoded by the nucleotide sequence shown in FIG. 1B (SEQ ID NO:2). The light chain of the humanized RP215 antibody is encoded by the nucleotide sequence shown in FIG. 1D (SEQ ID NO:4). FIGS. 1A and 1C show the corresponding amino acid sequences of the heavy and light chains, respectively, of the humanized RP215 antibody (SEQ ID NOS:1 and 3, respectively). FIG. 2B shows the amino acid sequence of the heavy chain ($V_H$) of the humanized RP215 antibody (SEQ ID NO:5), and FIG. 2C shows the amino acid sequence of the light chain ($V_L$) of the humanized RP215 antibody (SEQ ID NO:6).

With reference to FIG. 2A, the partial structure of an example embodiment of a nucleotide vector encoding an RP215 CAR is illustrated. In the example embodiment, the RP215 CAR comprises from N-terminal to C-terminal a signal peptide 110, a $V_H$ fragment of an RP215 monoclonal antibody 112, a linker 114, a $V_L$ fragment of an RP215 monoclonal antibody 116, a hinge region 118, a transmembrane domain 120, a costimulatory domain 122, and a CD3 zeta subunit domain 124.

The signal peptide 110 is used to direct the translated RP215 CAR into the endoplasmic reticulum, so that the antigen binding domain of the RP215 CAR will be expressed on the surface of an immune cell. In the illustrated embodiment, the signal peptide 110 comprises the interleukin 2 signaling sequence (IL2ss), which is used to direct the CAR for cell membrane expression in an immune cell. In alternative embodiments, any signaling domain that directs the CAR to be appropriately expressed in a membrane of an immune cell could be used.

The antigen binding domain in the exemplary embodiment of FIG. 2A comprises the $V_H$ region 112, linker 114 and $V_L$ region 116 that together are an scFv of an RP215 monoclonal antibody. In the exemplary embodiment described and characterized herein, the antigen binding domain of the RP215 CAR comprises the scFv of a humanized RP215 antibody, having the $V_H$ and $V_L$ regions of the humanized RP215 antibody having SEQ ID NOS:5 and 6, respectively shown in FIGS. 2B and 2C, joined by a peptide linker.

In alternative embodiments, the sequences of the $V_H$ and $V_L$ regions of antigen binding fragment of the RP215 CAR (i.e. the scFv of RP215) could be the $V_H$ and $V_L$ regions, respectively, of any other humanized RP215 antibody.

In alternative embodiments, any suitable peptide linker sequence could be used to join the $V_H$ and $V_L$ regions of the scFV of the RP215 antibody in the RP215 CAR. Some parameters limiting the nature of a linker used in an scFV are that it be sufficiently soluble and that it allow the $V_H$ and $V_L$ regions of the antibody to bind to the target antigen.

In example embodiments, the linker used in the scFV of the RP215 antibody can be between about 10 and about 25 amino acids in length, including any value therebetween e.g. 11, 12, 13, 14, 15, 16, 17, 18, 19, 20, 21, 22, 23 or 24 amino acids in length. In some embodiments, the linker used in the scFV of the RP215 antibody is rich in glycine. In some embodiments, the linker used in the scFV of the RP215 antibody includes a plurality of serine and/or threonine residues, to enhance the solubility of the linker.

While in the illustrated embodiment, the linker region of the scFv joins the C-terminus of the $V_H$ portion of the RP215 antibody with the N-terminus of the $V_L$ portion of the RP215 antibody, in alternative embodiments, the linker region of the scFv could join the C-terminus of the $V_L$ portion of the RP215 antibody with the N-terminus of the $V_H$ portion of the RP215 antibody.

The antigen binding domain of the RP215 CAR enables immune cells that have been genetically engineered with a nucleotide vector encoding the RP215 CAR to specifically bind to CA215, which is expressed in cancer cells.

In some embodiments, the RP215 CAR binds to a carbohydrate-associated epitope in the cancer cell surface expressed tumor-associated antigen CA215. In some embodiments, the antigen binding domain of the RP215 CAR has a specificity and affinity for binding CA215 that is comparable to murine RP215. In some embodiments, the antigen binding domain of the RP215 CAR has a specificity and affinity for binding to CA215 that is comparable to humanized RP215.

In some embodiments, the antigen binding domain of the RP215 CAR has a binding affinity for CA215 associated with a dissociation constant ($K_D$) of at least $10^{-7}$ M, $10^{-8}$ M $10^{-9}$ M or $10^{-10}$ M, or any value within that range.

In the illustrated embodiment, a hinge region 118 is provided that extends between the antigen binding domain of the RP215 CAR (110, 112, 114) and the transmembrane domain 120. Hinge region 118 ensures that the antigen binding domain (i.e. the scFv of RP215 in the illustrated embodiment) is free to bind to CA215 in vivo. In the illustrated embodiment, hinge region 118 comprises the hinge domain of a CD8 molecule. In alternative embodiments, any suitable hinge region that allows the antigen binding domain (e.g. the scFv of RP215) of the RP215 CAR to bind to CA215 could be used.

In the illustrated embodiment, the transmembrane domain from a CD8 molecule is used to provide transmembrane domain 120. In alternative embodiments, any suitable transmembrane domain that allows the antigen binding domain and the intracytoplasmic domain of the RP215 CAR to be coupled together and extend through the cell membrane of an immune cell could be used.

In the illustrated embodiment, the RP215 CAR comprises a 4-1BB costimulatory domain 122 present on the intracellular portion of the protein. Without being bound by theory, it is believed that the 4-1BB costimulatory domain costimulates T cells to improve CAR-T persistence in vivo. In some embodiments, the 4-1BB costimulatory domain could be omitted. In some embodiments, the 4-1BB costimulatory domain could be replaced by a different domain that improves CAR-T persistence in vivo.

In the illustrated embodiment, the CD3 zeta subunit domain 124 performs the function of signaling within T-cells. Without being bound by theory, once CA215 is bound by the antigen binding domain of the RP215 CAR, the CD3 zeta subunit domain transmits an activation signal to the T-cell, to initiate killing of the cell expressing CA215.

Some embodiments of the invention provide a nucleotide vector for the introduction and expression of humanized RP215 monoclonal antibody or a fragment thereof in immune cells, such as T cells, to confer binding specificity for CA215 on that immune cell. The nucleotide vector comprises a nucleic acid molecule encoding an RP215 CAR construct. In some embodiments, the vector is a vector suitable for transduction into a target cell, such as a T cell. In some embodiments, the vector is a vector suitable to be introduced into a target cell, such as an immune cell and including a T cell, by any available means of genetic engineering.

Figure 3:
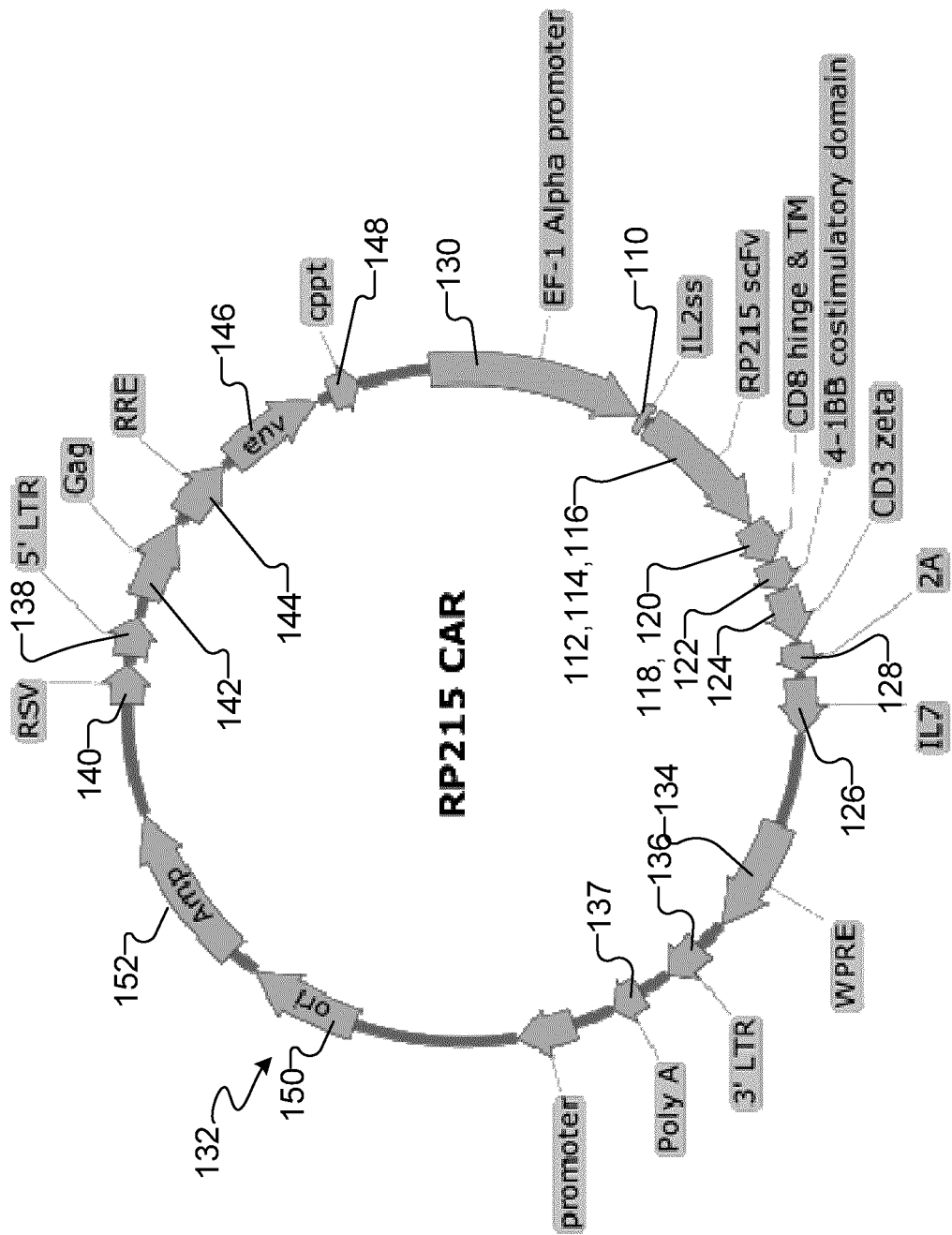
FIG. 3 is a schematic diagram showing schematically an example embodiment of a complete recombinant RP215 CAR-T lentiviral vector construct. The amino acid sequence encoded by the RP215 CAR-T nucleotide vector construct comprises SEQ ID NO:7. In this example embodiment, the gene sequence of the RP215 CAR nucleotide vector construct is present in the form of a plasmid that can be used as a transfer plasmid to produce lentivirus capable of introducing the nucleotide vector capable of expressing the RP215 CAR into an immune cell, e.g. a T cell.

In one example embodiment, the nucleotide vector comprises a lentiviral vector encoding an RP215 CAR construct as shown in FIG. 3. The exemplary nucleotide vector construct encodes a polypeptide having the amino acid sequence of SEQ ID NO:7. The polypeptide having the amino acid sequence of SEQ ID NO:7 is a fusion protein comprising an RP215 CAR and a cytokine 126, separated by a self-cleavable peptide 128 so that the two proteins can be separated after translation.

In some embodiments, the nucleotide vector provides for expression of an RP215 CAR in a T cell after that T cell has been transduced with a suitable nucleotide vector construct that is capable of expressing an RP215 CAR.

In some embodiments, a nucleotide vector capable of expressing an RP215 CAR in a suitable host cell is provided. In some embodiments, the nucleotide vector is provided as a lentiviral vector. FIG. 2A shows schematically a portion of the nucleotide sequence of an exemplary RP215 CAR lentiviral vector, which is an example of a nucleotide vector capable of expressing an RP215 CAR. FIG. 3 shows schematically the full structure of a nucleotide vector capable of expressing an RP215 CAR in a suitable host cell, in which the nucleotide vector comprises a transfer plasmid for use in a lentiviral gene therapy system.

In some embodiments, the nucleotide vector capable of expressing an RP215 CAR comprises nucleic acid sequences encoding the signal peptide 110, $V_H$ fragment 112, linker 114, $V_L$ fragment 116, hinge region 118, transmembrane domain 120, costimulatory domain 122, and CD3 zeta subunit domain 124 described above.

In some embodiments, with reference to FIG. 2A, the nucleotide vector capable of expressing an RP215 CAR further encodes a cytokine 126, which without being bound by theory may be important for T cell development. In some embodiments, the nucleotide vector encodes the cytokine 126 so that it will be expressed as a C-terminal fusion protein with the RP215 CAR. In some such embodiments, the nucleotide vector capable of expressing an RP215 CAR further encodes a self-cleavage peptide 128 that interposes the RP215 CAR and the cytokine 126, so that after translation thereof, the RP215 CAR will self-cleave from the cytokine 126. A self-cleavage peptide sequence allows the expression of two proteins from the same RNA. After translation, the peptide containing the two proteins will self-cleave at the self-cleavable peptide sequence region.

In some embodiments, the cytokine 126 is IL-7, or another interleukin such as IL-15. In alternative embodiments, any desired cytokine could be used, or additional cytokines separated by additional self-cleavage peptides could be used.

In the illustrated embodiment, the self-cleavage peptide 128 comprises 2A. In alternative embodiments, any suitable self-cleaving peptide sequence could be used.

In some embodiments, the nucleotide vector capable of expressing an RP215 CAR comprises a promoter sequence 130, to drive expression of the RP215 CAR in vivo. In the illustrated embodiment of FIG. 2A, the promoter is the EF-1 alpha promoter. In alternative embodiments, any suitable promoter can be used.

With reference to FIG. 3 in which like reference numerals refer to like elements of FIG. 2A, additional elements present on an example embodiment of a nucleotide vector capable of expressing an RP215 CAR are shown. In the illustrated example embodiment of FIG. 3, the nucleotide vector capable of expressing an RP215 CAR comprises a lentiviral plasmid 132. Lentiviral plasmid 132 is a transfer plasmid that can be used to transfect eukaryotic cells to produce viruses bearing the nucleotide sequences encoding the RP215 CAR, which can in turn be used to carry out genetic engineering of suitable immune cells of a subject, for example T cells, to produce immune cells that express the RP215 CAR.

In some embodiments, a post-transcriptional regulatory element is provided on the nucleotide vector. In the illustrated embodiment, the post-transcriptional regulatory element is Woodchuck hepatitis virus post-transcriptional regulatory element 134, which stimulates the expression of transgenes via increased nuclear export. In some embodiments, any suitable post-transcriptional regulatory element can be used.

In some embodiments, a 3' LTR 136 is provided on the nucleotide vector capable of expressing an RP215 CAR, to terminate transcription by the addition of a poly-A tract 137 just after the R sequence.

In some embodiments, a 5' LTR 138 is provided on the nucleotide vector capable of expressing an RP215 CAR, to act as a promoter for RNA polymerase II.

In some embodiments, the nucleotide vector capable of expressing an RP215 CAR contains a transcription promoter. In the illustrated embodiment, the transcription promoter is a constitutive promoter. In the illustrated embodiment, the transcription promoter is a Rous Sarcoma Virus (RSV) constitutive promoter 140.

In some embodiments, the nucleotide vector capable of expressing an RP215 CAR contains a Gag sequence 142. Gag is a precursor structural protein of the lentiviral particle containing the matrix, capsid and nucleocapsid components.

In some embodiments, the nucleotide vector capable of expressing an RP215 CAR contains a Rev Response Element (RRE) 144, which is a sequence to which the Rev protein binds.

In some embodiments, the nucleotide vector capable of expressing an RP215 CAR contains a gene encoding VSV-G envelope protein (indicated as "env" 146).

In some embodiments, the nucleotide vector capable of expressing an RP215 CAR contains a central polypurine tract (cppt, 148), which is a recognition site for proviral DNA synthesis that increases transduction efficiency and transgene expression.

In some embodiments, the nucleotide vector capable of expressing an RP215 CAR contains an origin of replication (on, 150) to allow for replication of the plasmid.

In some embodiments, the nucleotide vector capable of expressing an RP215 CAR contains an antibiotic resistance marker, which in the illustrated embodiment is an ampicillin resistance marker, Amp 152.

In some embodiments, an immune cell expressing an RP215 CAR is provided. In some embodiments, an RP215 CAR is expressed on the surface of a suitable immune cell, e.g. a T cell or a natural killer, NK, cell.

In some embodiments, an RP215 CAR is present on the surface of a T cell or an NK cell and the RP215 CAR binds to CA215 expressed on the surface of cancer cells. In some embodiments, the RP215 CAR binds to CA215 expressed on the surface of cells with a specificity and an affinity comparable to that of humanized RP215 antibody. The RP215 CAR binds to CA215 on cancer cells, thereby mediating killing of the cancer cells by the T cell or NK cell.

In some embodiments, lentivirus bearing the nucleotide vector capable of expressing an RP215 CAR are used to carry out gene therapy. Suitable immune cells, for example T cells, are harvested from either a cancer patient (for autologous CAR-T therapy) or from a healthy subject (for allogenic CAR-T therapy). The T cells are transduced with the nucleotide vector capable of expressing the RP215 CAR via a lentiviral vector. The genetically engineered T cells capable of expressing the RP215 CAR are then introduced into the body of the cancer patient to selectively kill cancer cells expressing CA215.

In some embodiments, the nucleotide vector capable of expressing an RP215 CAR is a lentiviral vector, and the lentiviral vector is introduced into the T cells as RNA via a lentivirus vector. Once inside the T cells, the RNA is reverse-transcribed to yield DNA, which integrates with the genome of the T cell via the viral integrase enzyme.

Some embodiments of the present invention are directed to a genetically modified T cell capable of expressing an RP215 CAR. In some embodiments, the genetically modified T cell is obtained via transduction with a nucleotide vector capable of expressing an RP215 CAR. In some embodiments, the genetically modified T cell is produced by any suitable genetic modification technique, e.g. gene editing using clustered regularly interspaced short palindromic repeats ("CRISPR")/Cas9 technology can be carried out, so that the genetically modified T cell will produce an RP215 CAR. This will cause the immune cell to express RP215 CAR incorporating an antigen-binding fragment of RP215 that binds to CA215. In some embodiments, the immune cells are T cells or natural killer (NK) cells.

Some embodiments relate to methods of treating cancer. In one example embodiment, a method of treating cancer comprises: i) genetically modifying T cells obtained from a subject with suitable nucleotide vectors encoding an RP215 CAR construct; and ii) introducing the genetically modified T cells into the patient suffering from cancer. In some embodiments, the T cells are obtained from the patient suffering from cancer. In some embodiments, the T cells are obtained from a healthy subject, genetically modified, and then introduced into a patient suffering form cancer.

Upon transduction or genetic engineering to introduce a nucleotide vector capable of expressing an RP215 CAR into immune cells such as T cells or NK cells, the genetically modified immune cells will then express the scFv chain of humanized RP215 antibody on their surface, which acts as an antigen binding domain. This immunoglobulin chain will bind to CA215 expressed on the surface of cancer cells, and will result in cytotoxic killing of cancer cells via the T cells. Therefore, the RP215 CAR-T system can be utilized for therapeutic applications for treatment of some human cancers.

In some embodiments, a plurality of immune cells, e.g. T cells or NK cells, that express an RP215 CAR construct can be isolated and stored in a frozen state, e.g. at −80° C. Such cells can then be thawed at a future date for introduction into a patient who has a subsequent relapse of cancer during his or her lifetime.

In view of the widespread expression of CA215 on the surface of many human cancer cells, it can be soundly predicted that the RP215 CAR construct has broad potential therapeutic applications in all human cancers associated with a high level of expression of CA215. CA215 has been found to be present in a number of different types of cancers, including of the ovary, cervix, endometrium, colon, stomach, intestine, esophagus, breast, and lung, as well as being present in liver and kidney cancer cell lines as well as lymphoma, melanoma, neuroblastoma, bone, and prostate cancer cell lines: see U.S. Pat. No. 814,373 to Lee.

In some embodiments, the cancer is neuroblastoma, lymphoma, melanoma, or cancer of the colon, stomach, intestine, esophagus, liver, kidney, lung, bone, breast, ovary, cervix, endometrial tissue, or prostate.

In some embodiments, the cancer is a cancer that expresses the cancer marker CA215.

While the exemplary embodiments described herein have been described with reference to human CA215, similar embodiments with appropriate modifications could be used in other mammals that suffer from cancers involving expression of CA215 on the surface of the cancer cell.

While in one exemplary embodiment described herein a lentiviral vector system has been described for use in the transduction of immune cells to express an RP215 CAR, in alternative embodiments, any suitable retroviral vector system could be used to carry out such transduction.

EXAMPLES

Specific embodiments of the invention are described with reference to the following examples, which are intended to be illustrative and not limiting in nature.

Example 1.0—Preparation of Nucleotide Vector Capable of Expressing RP215—Target Plasmid Using the sequences of the $V_H$ and $V_L$ portions of the humanized RP215 monoclonal antibody, the full length of RP215 CAR nucleotide cassette construct is synthesized according to the established frame and scheme, and then sub-cloned into a lenti-Puro vector transfer plasmid using standard molecular biology techniques. The insert was confirmed by Sanger sequencing.

Figure 4:
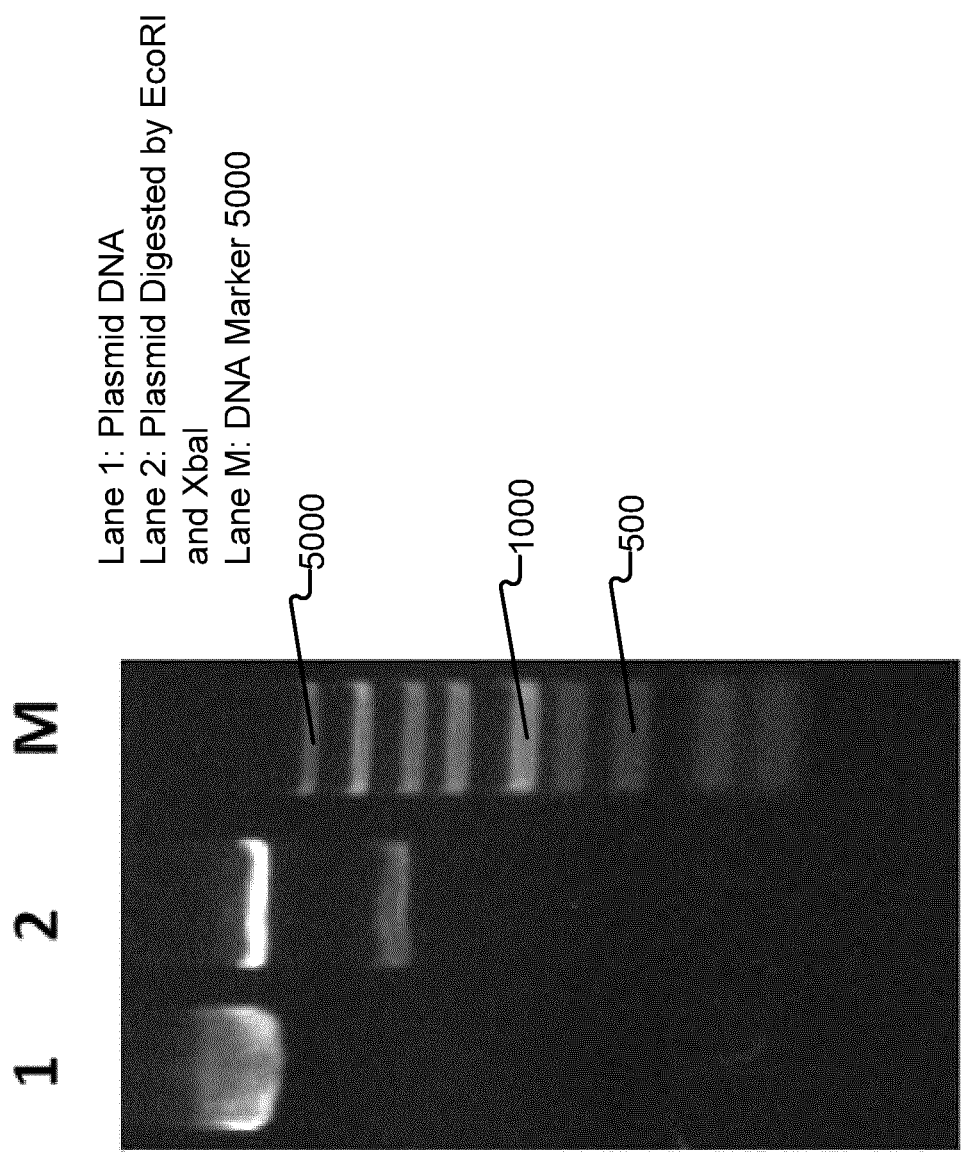
FIG. 4 shows the molecular weights of DNA fragments produced by digesting the exemplary RP215 CAR nucleotide vector construct shown in FIG. 3 with restriction endonucleases EcoRI and XbaI.

The resulting construct is validated by endonuclease digestion, as shown in FIG. 4. The recombinant vector was digested with EcoRI-XbaI, yielding the expected 2079 bp fragment.

Example 2.0—Preparation of Lentivirus Containing RP215 CAR Transfer Plasmid

HEK293T cells (human embryonic kidney cells 293) are transfected to produce lentiviruses suitable for use in the genetic engineering of T cells to produce RP215 CAR. HEK293T cells are cultured overnight in complete culture medium, and are transfected with the RP215 transfer plasmid (plasmid 132), along with packaging plasmids including pGP (encoding Gag and Pol) and pVSVG envelope plasmid (encoding Env, VSV-G) to form lentiviral vector particles. The DNA is mixed with polyethylenimine (PEI) and then cultured with the cells. After 48 hours, supernatant is harvested and filtered to produce the virus stock, which can be aliquoted and stored at −80° C.

Example 3.0—Lentivirus Titration

Lentiviral copy number is determined (see e.g. Barczak et al., Mol. Biotechnol., 2015, 57:195-200, which is hereby incorporated by reference herein). HT1080 cells (a fibrosarcoma cell line) are grown, and serial dilutions of concentrated lentivirus are added to the cells together with Polybrene (hexadimethrine bromide). Virus and cells are incubated for 96 hours, then cells are washed with PBS. Genomic DNA is extracted using a Genomic DNA Purification Kit from Lifetech, and its concentration determined by NanoDrop 2000.

A standard curve for WPRE (woodchuck hepatitis virus post-transcriptional regulatory element), used as the lentiviral-specific gene, and ALB (albumin), used as a single copy reference gene, is prepared for real-time qPCR using pUC-WPRE and pUC-ALB. PCR is carried out for 40 cycles.

The primers used for PCR and detection were as follows:

| Primers | 5'-3' | Fluorescent group |
|---|---|---|
| WPRE_ forward | GGCACTGACAATTCCGTGGT (SEQ ID NO: 8) | N.A. |
| WPRE_ reverse | AGGGACGTAGCAGAAGGACG (SEQ ID NO: 9) | N.A. |
| WPRE_ probe | ACGTCCTTTCCATGGCTGCTCGC (SEQ ID NO: 10) | 5'-FAM-BHQ1-3' |
| Alb_ forward | GCTGTCATCTCTTGTGGGCTGT (SEQ ID NO: 11) | N.A. |
| Alb_ reverse | ACTCATGGGAGCTGCTGGTTC (SEQ ID NO: 12) | N.A. |
| Alb_ probe | CCTGTCATGCCCACACAAATCTCTCC (SEQ ID NO: 13) | 5'-FAM-BHQ1-3' |

Figure 5A:
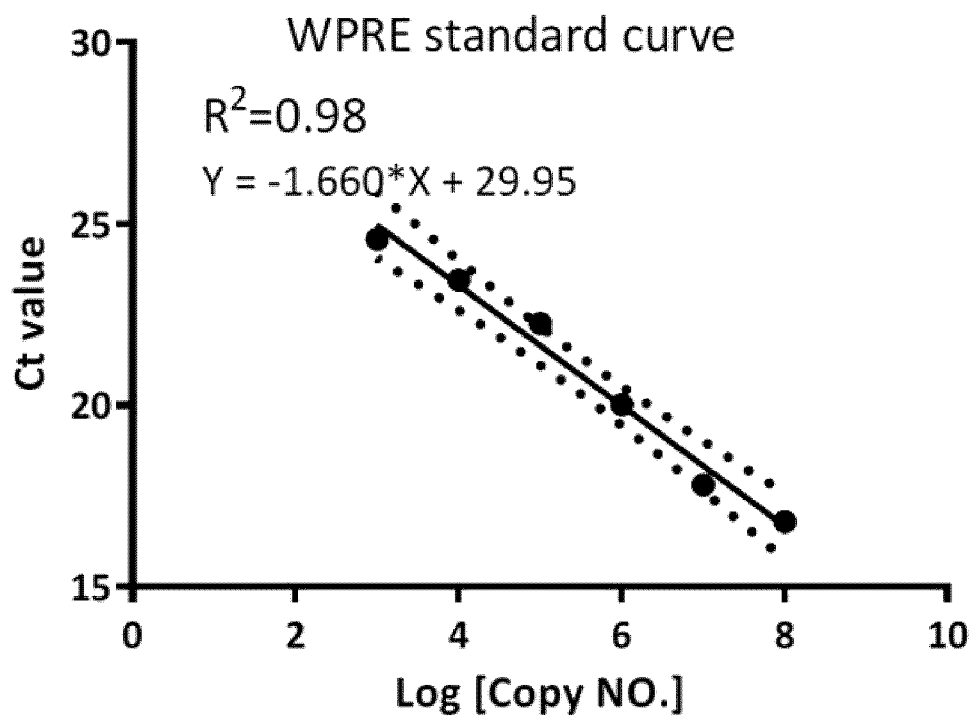
FIGS. 5A and 5B show qPCR standard curves used to reveal titers by lentivirus titration.
Figure 5B:
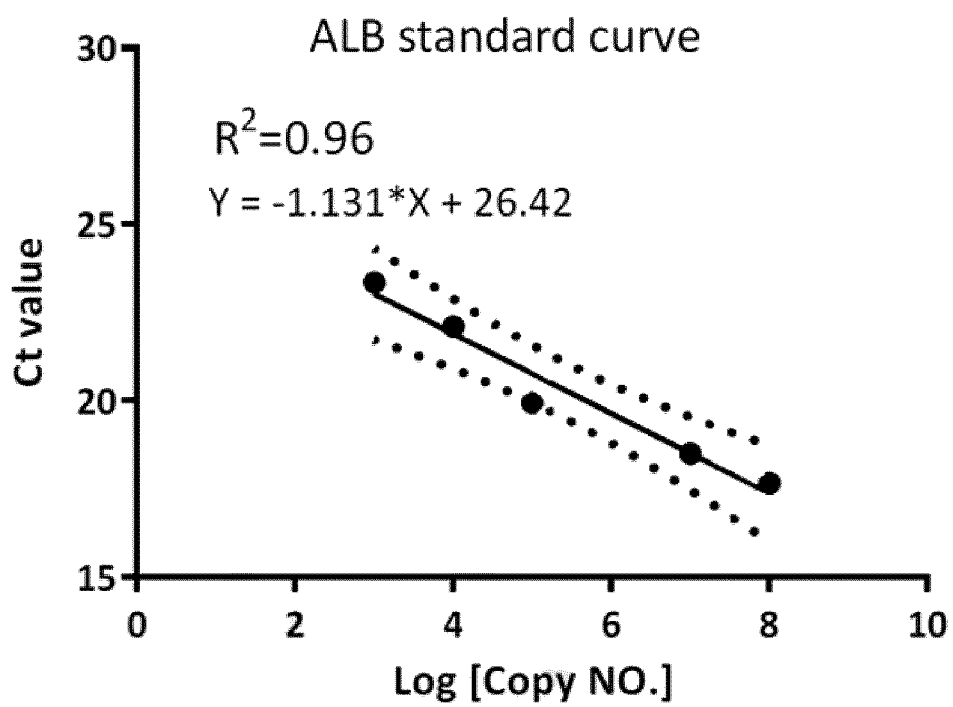

The standard curves of Ct value (cycle threshold) versus copy number obtained for WPRE and ALB are presented in FIGS. 5A and 5B. Results for determination of Ct value are presented in Table 1.

TABLE 1

| | Ct value of the virus. | | | |
|---|---|---|---|---|
| | WPRE | | ALB | |
| RP215 | 23.17 | 23.74 | 19.96 | 19.92 |

The virus titer calculation is done using the following formula:

$$\text{Lentivirus Titer } TU/\text{mL} = \frac{(\text{Copy}WPRE/\text{Copy } ALB * 2) * \text{Cell No.}}{\text{Volume of virus}}$$

and was determined to be $4.15 \times 10^{12}$ TU/mL.

This example demonstrates that lentiviral vectors were prepared. The results of lentiviral titration indicated that a lentiviral vector bearing the RP215 CAR transfer plasmid was successfully constructed with a high titer.

Example 4.0—Isolation and Preparation of Primary RP215 CAR T-Cells

Lymphoprep™ density gradient medium is used to separate PBMC (peripheral blood mononuclear cells including T cells) from other components of whole blood samples. Magnetic Dynabeads™ CD3 are used to isolate CD3⁺ T cells, and resulting cells are washed with PBS and resuspended and cultured in X-vivo 15 medium.

Lentiviral vector particles were used to transduce the T cells, with an MOI (multiplicity of infection) of 20. Lentiviral vector particles are defrosted and mixed with Polybrene (hexadimethrine bromide) and isolated T cells. After centrifugation, the cell pellet is harvested, resuspended in fresh medium, and cells are cultured.

Example 5.0—Validation of Insertion of RP215 CAR in Transduced T Cells

RT qPCR was carried out to determine the number of copies of nucleotide vector encoding RP215 in lentivirus-transduced T cells. Genomic DNA is extracted from transduced T cells using a Genomic DNA Purification Kit (Lifetech). DNA concentration is determined using Nanodrop 2000.

pUC-LTR and pUC-ALB plasmids are prepared, and serial dilutions are made to prepare the standard curve for RT qPCR. Primers used for ALB are those of SEQ ID NOS:11, 12 and 13. Primers used for LTR are as follows below. PCR is carried out for 40 cycles.

| Primer | Sequence (5'-3') | Fluorophore |
|---|---|---|
| LTR F | TGACAGCCGCCTAGCATTTC (SEQ ID NO: 14) | None |
| LTR R | GCTCGATATCAGCAGTTCTTGAAG (SEQ ID NO: 15) | None |
| LTR Probe | CACGTGGCCCGAGAGCTGCATC (SEQ ID NO: 16) | 5'-FAM-BH Q1-3' |

ALB and LTR standard curves are generated to determine copy number for RP215 CAR validation in transduced T cells. After obtaining the Ct value, the Copy No. of RP215 CAR in the resultant recombinant T cells is calculated based on the formulation below.

$$\text{Average Copy No./cell} = \frac{Copy_{LTR}}{Copy_{ALB}} * 2$$

Figure 6A:
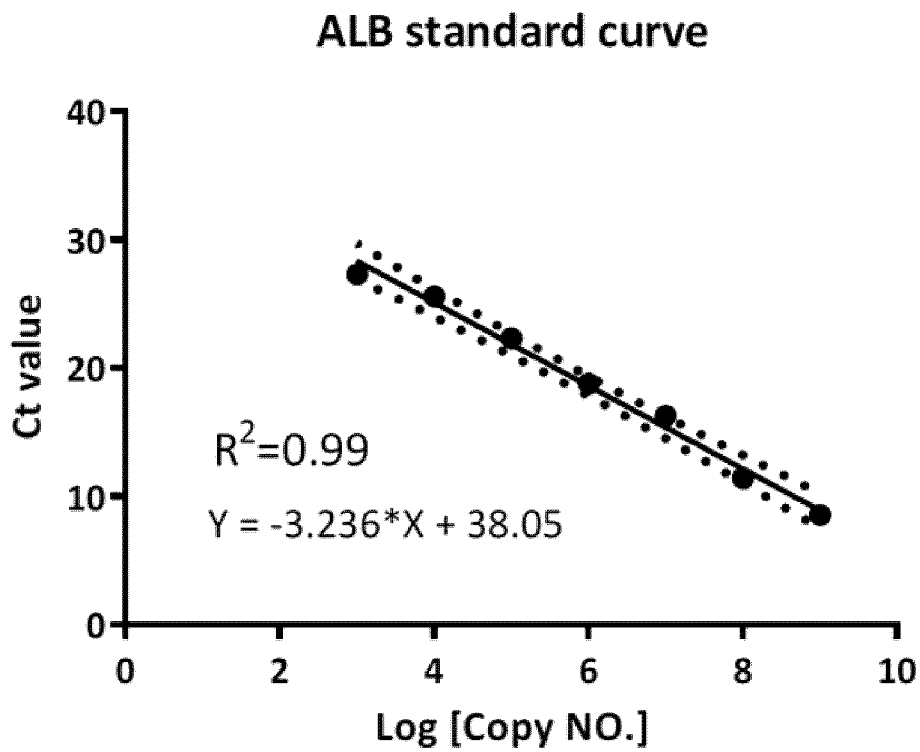
FIGS. 6A and 6B show validation of the insertion of the RP215 CAR nucleotide vector into transduced T cells by using a standard curve of Ct (cycle threshold) value to determine copy number.
Figure 6B:
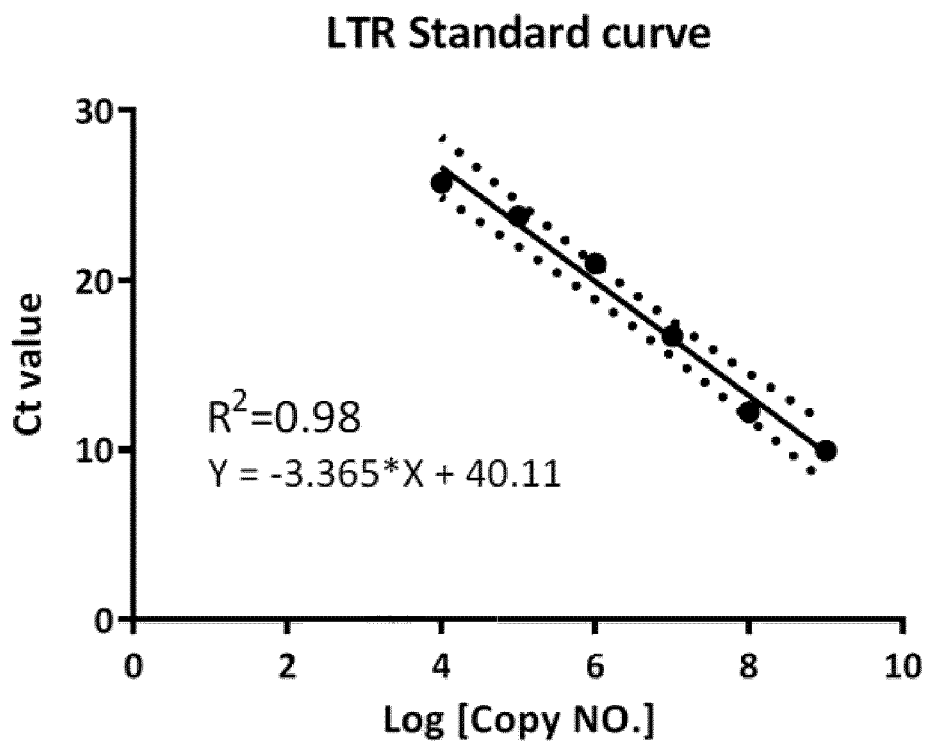

Results are presented in FIGS. 6A and 6B (ALB and LTR standard curves) and Table 2 (Ct value of samples). The average number of RP215 CAR gene copies in the genetically modified CAR-T cells was determined to be 3.6/cell.

TABLE 2

Ct value of samples.

| Sample | LTR | | ALB | |
|---|---|---|---|---|
| RP215 CAR-T cells | 26.63 | 26.75 | 25.86 | 26.12 |

These qPCR results showed that the genes of the constructed RP215 CAR nucleotide vector was successfully transduced into T cells.

Example 6.0—Lysis of Target Tumor Cells with RP215 CAR-T Cells

Tumor cells from a cell line of cervical carcinoma C33A (ATCC HTB-31) were employed as target tumor cells and cultured with RP215 CAR-T cells at three different E/T ratios under standard cell culture conditions. C33A cells are known to express CA215: see e.g. U.S. Pat. No. 8,143,373 to Lee.

Target C33A cells are grown to logarithmic phase, then lifted with trypsin and incubated overnight in assay wells. Prior to the assay, the assay wells are aspirated completely to remove culture and the cells are washed with sterilized PBS. RP215 CAR-T cells obtained in Example 4.0 are resuspended in RPMI 1640 medium without FBS and added to each assay well. Following 6 hours of co-culturing of both C33A tumor cells and RP215 CAR-T cells, the supernatant was harvested for determination of amount of lactate dehydrogenase (LDH) reduced using LDH detection reagent and the OD value was recorded. The percentage of target cell lysis was calculated as follows below. Maxi Lysis and Mini lysis were determined using four wells containing target C33A cells without RP215 CART cells, and cell lysis buffer was added to the Maxi lysis wells.

$$\text{Lysis\%} = \frac{(ODeach \text{ well} - ODmini \text{ lysis})}{ODmaxi \text{ lysis}}$$

Figure 7A:
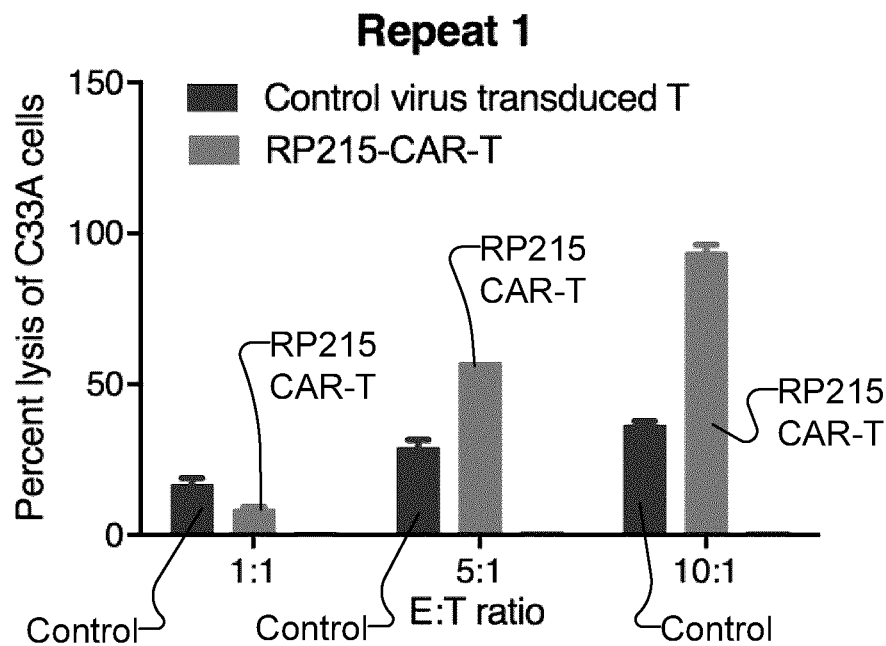
FIGS. 7A, 7B and 7C show the results of three repeats of a lysis assay, where genetically modified T cells comprising copies of the exemplary RP215 CAR nucleotide vector construct were co-cultured with tumor cells. Data for three repeats of CAR-T validation demonstrated by lysis of target tumor cells by RP215 CAR-T cells as measured by lactate dehydrogenase (LDH) assay are shown.
Figure 7B:
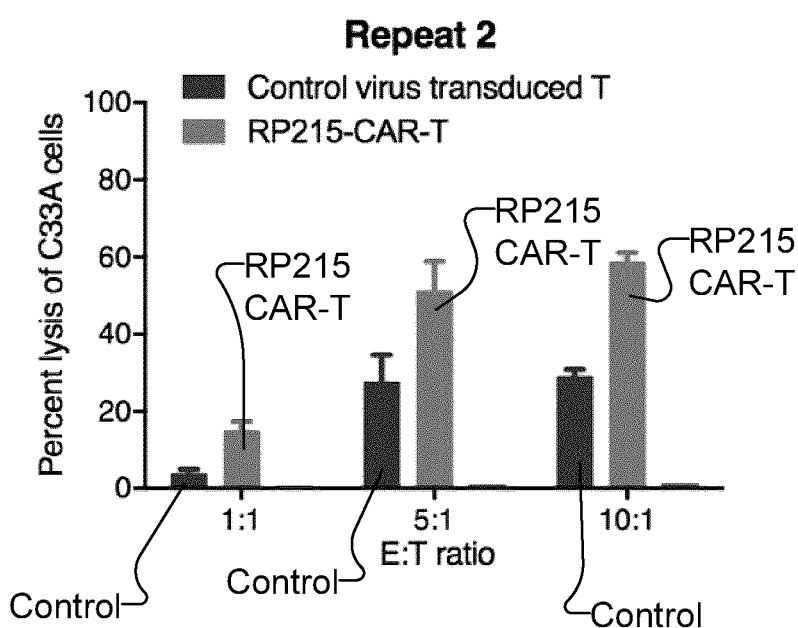
Figure 7C:
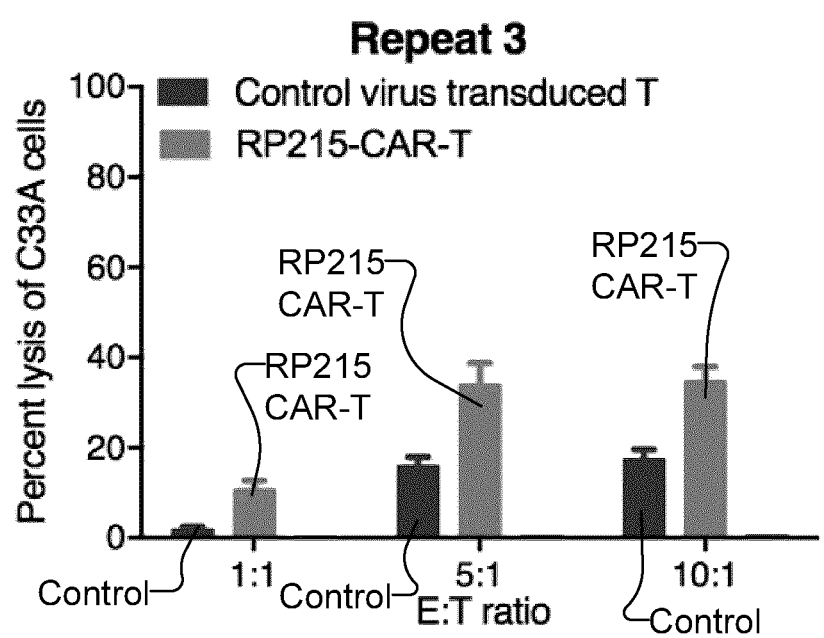
Figures 8A, 8B, 8C:
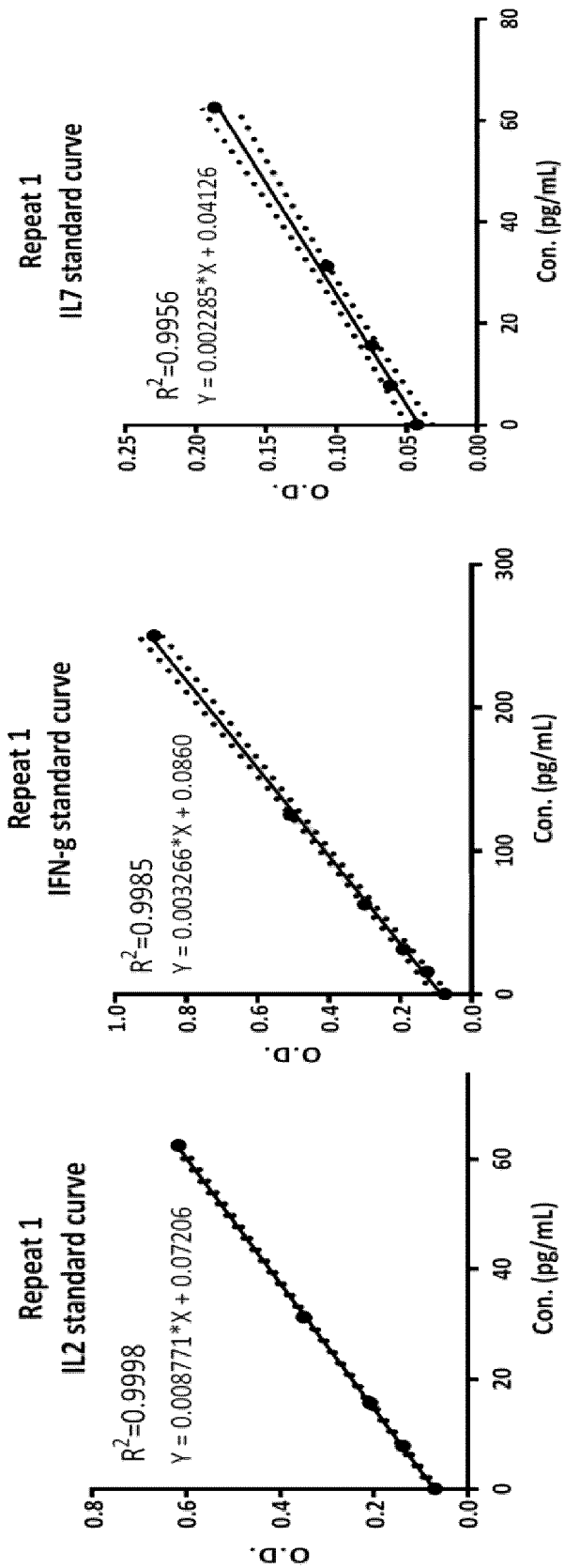
FIGS. 8A, 8B, 8C, 9A, 9B, 9C and 10A, 10B, 10C show standard curves for three separate repeats of the same experiment for IL-2, IFN-gamma and IL-7, respectively.
Figure 8D:
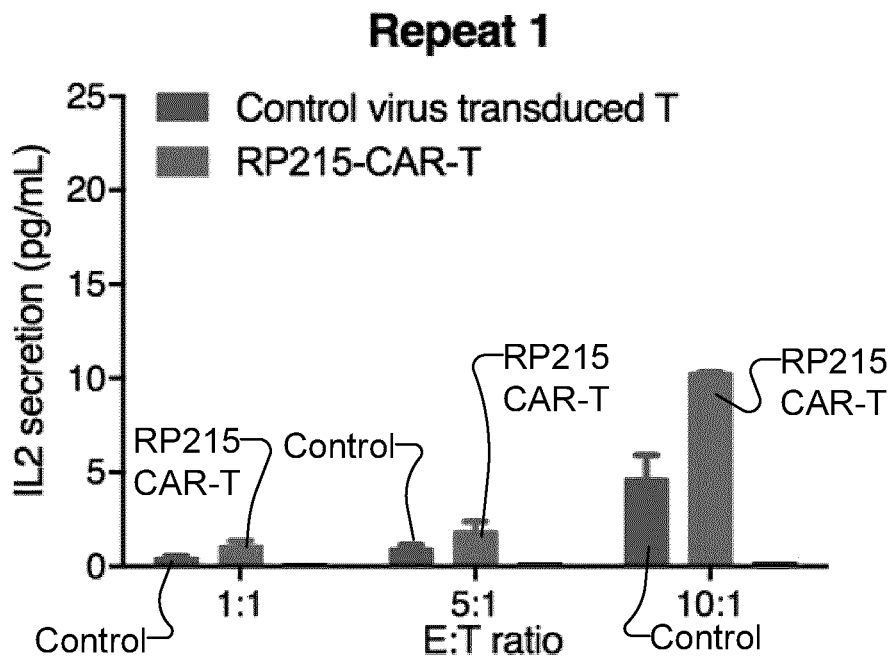
FIGS. 8D, 8E, 8F, 9D, 9E, 9F and 10D, 10E, 10F show the level of cytokines (D=IL-2, E=IFN-gamma and F=IL-7, respectively) produced by genetically modified T cells comprising copies of the exemplary RP215 CAR-T nucleotide vector construct, when the genetically modified T cells were co-cultured with cervical tumor (C33A) cells.
Figure 8E:
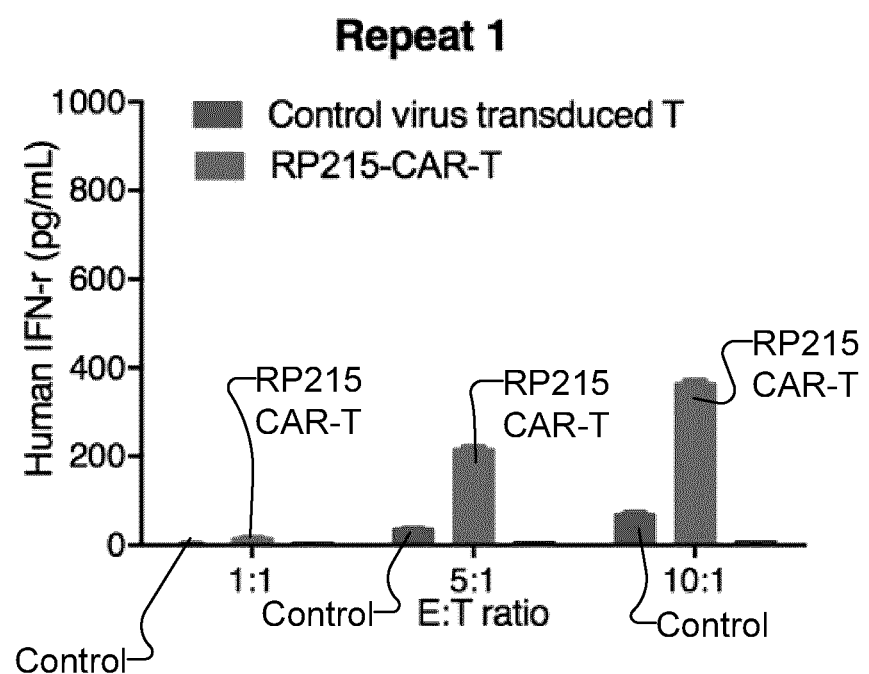
Figure 8F:
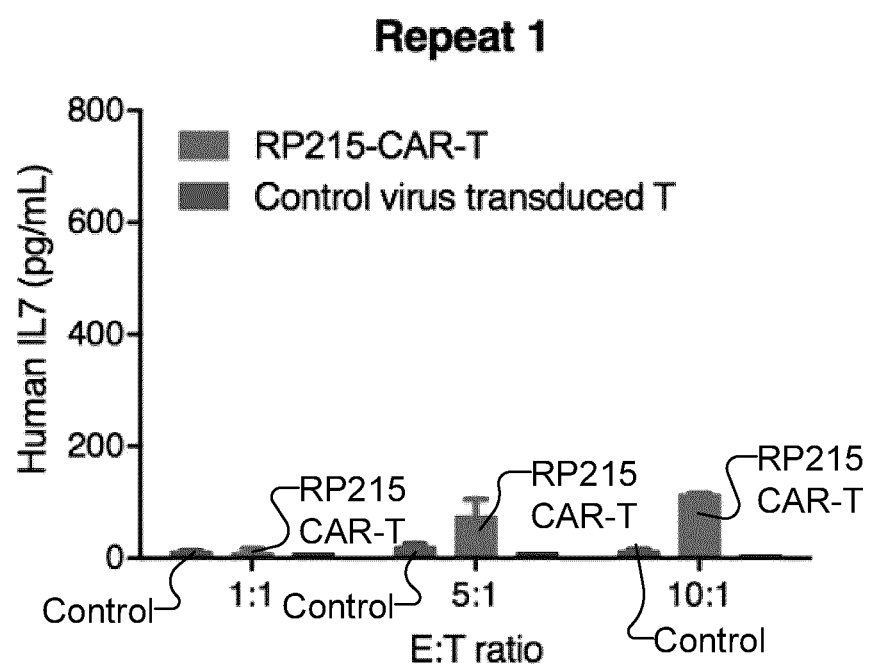
Figure 9A:
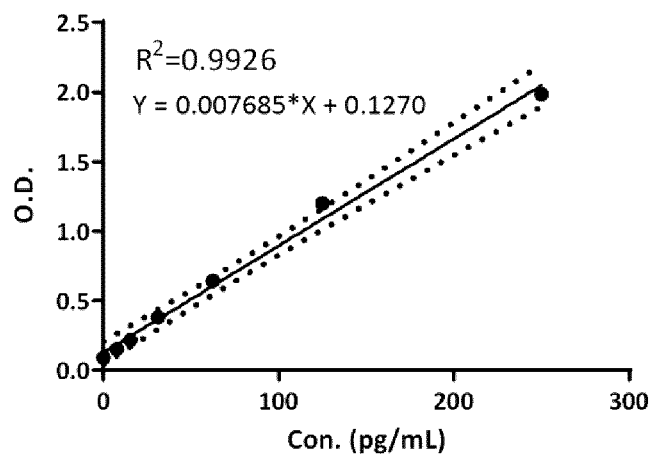
Figure 9B:
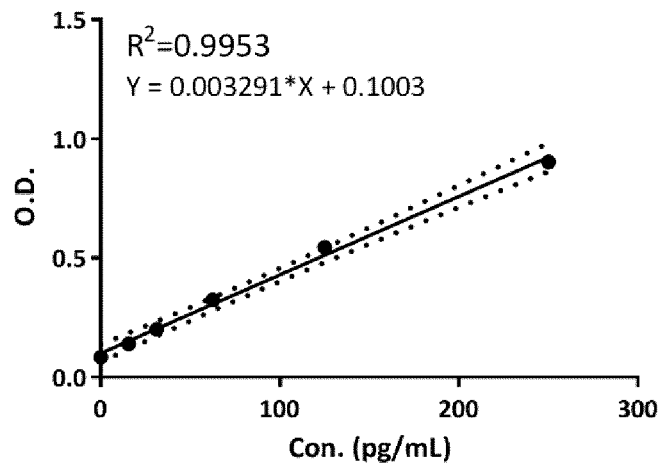
Figure 9C:
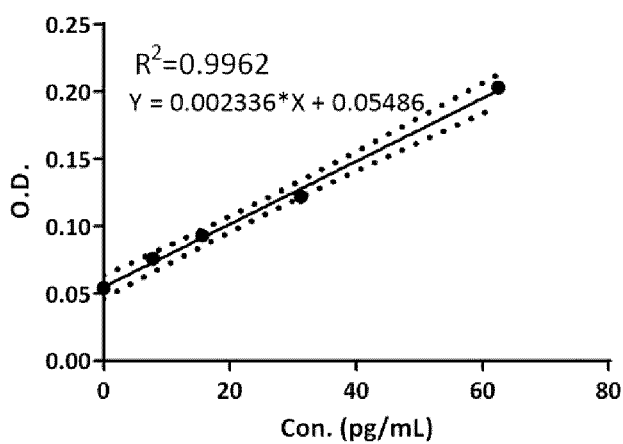
Figure 9D:
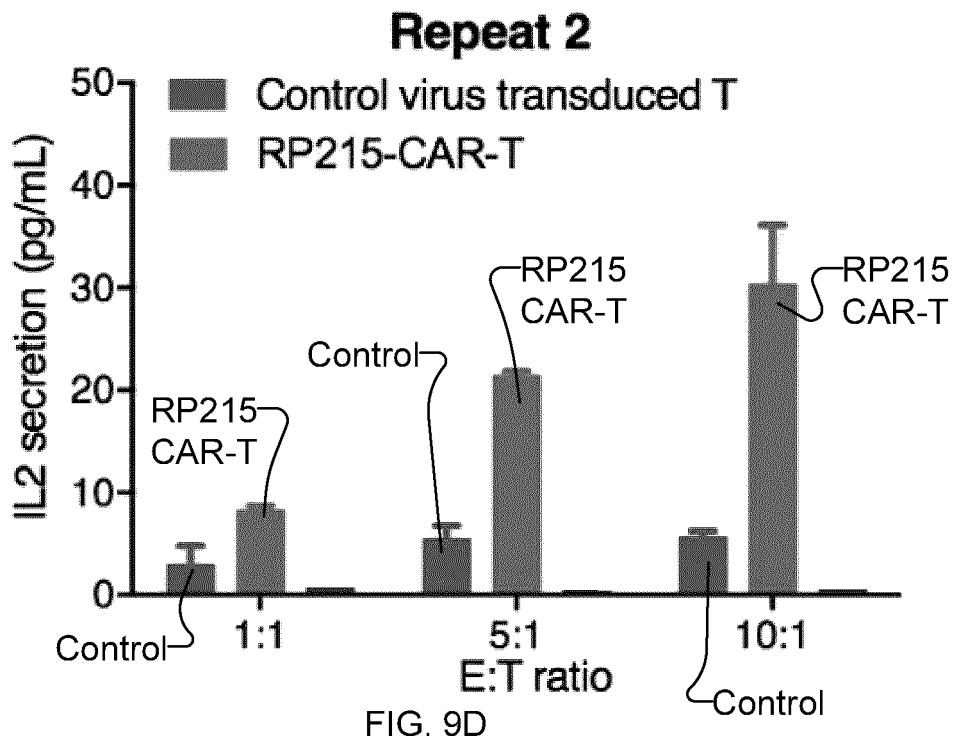
Figure 9E:
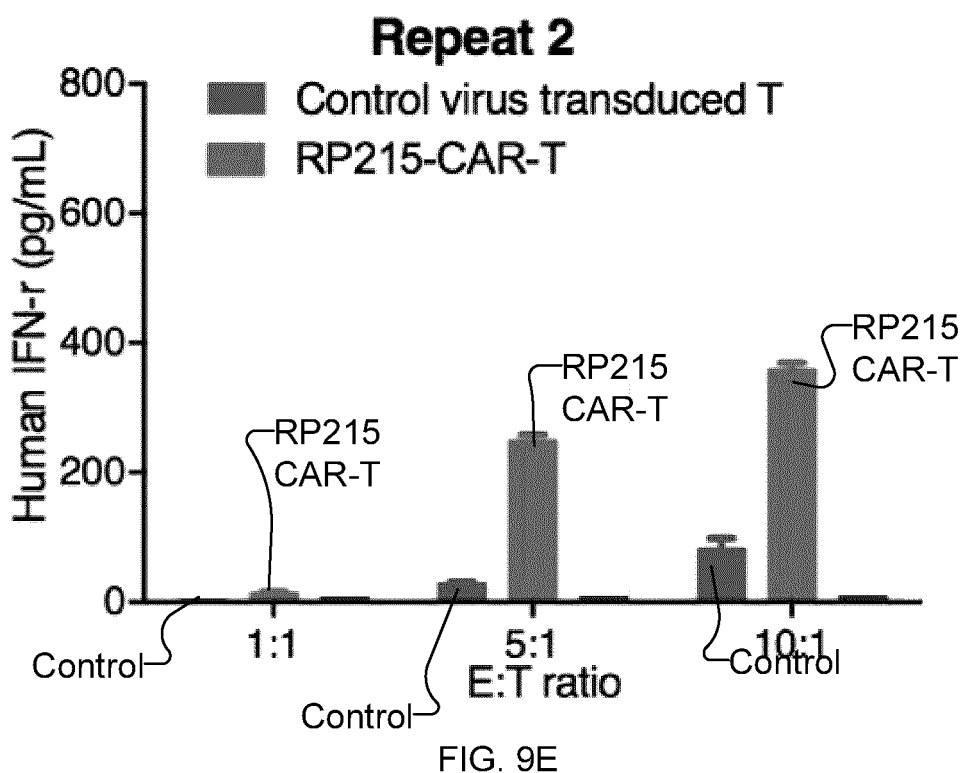
Figure 9F:
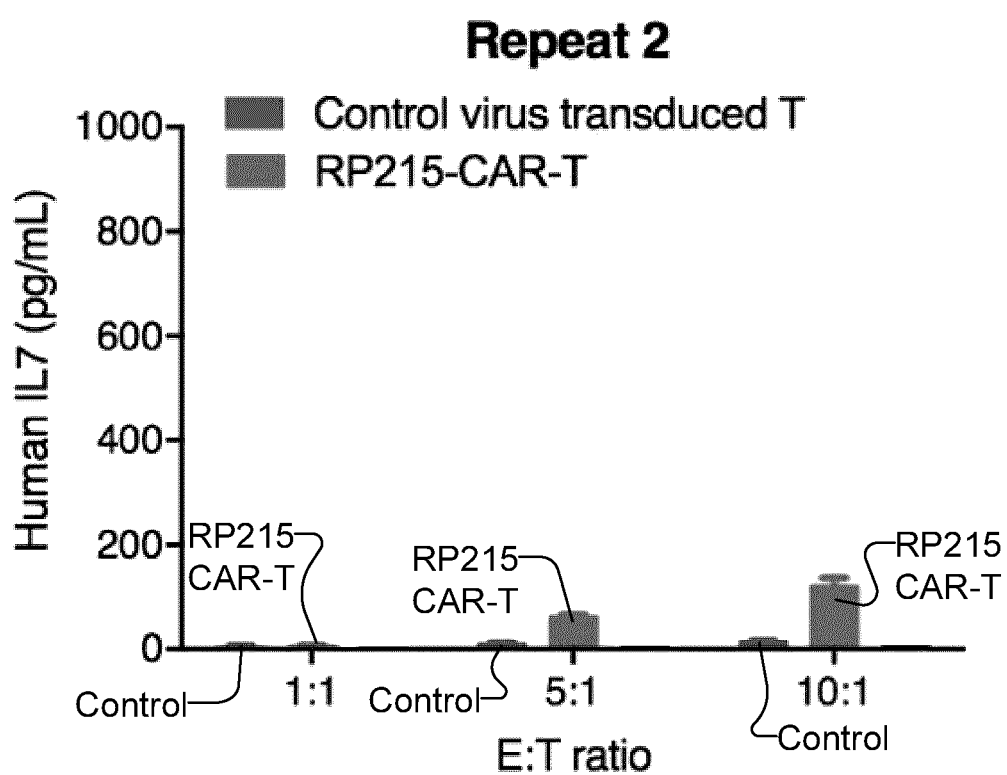
Figure 10A:
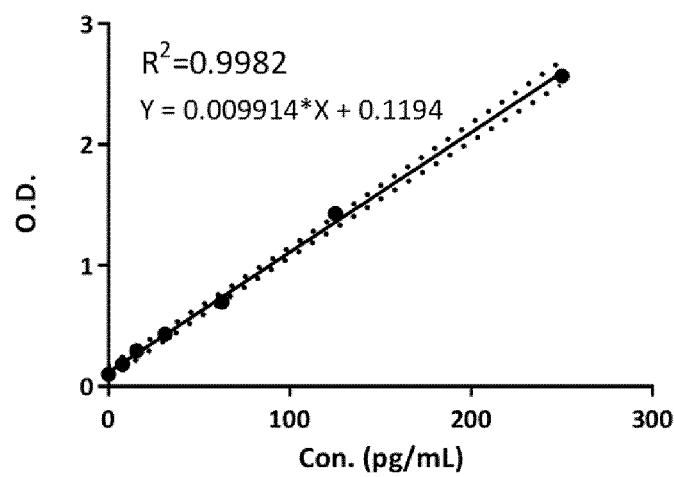
Figure 10B:
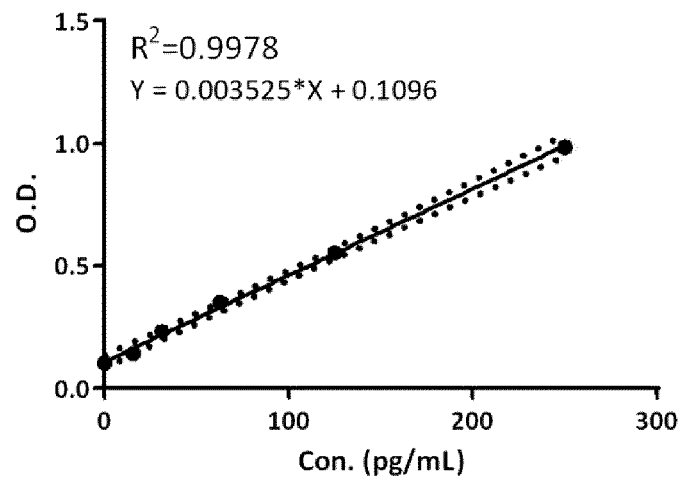
Figure 10C:
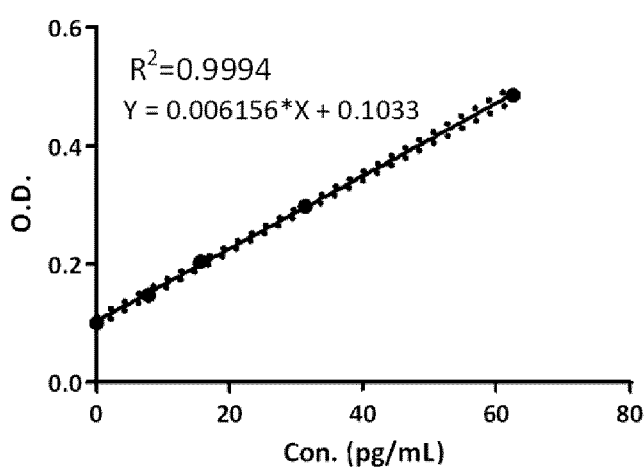
Figure 10D:
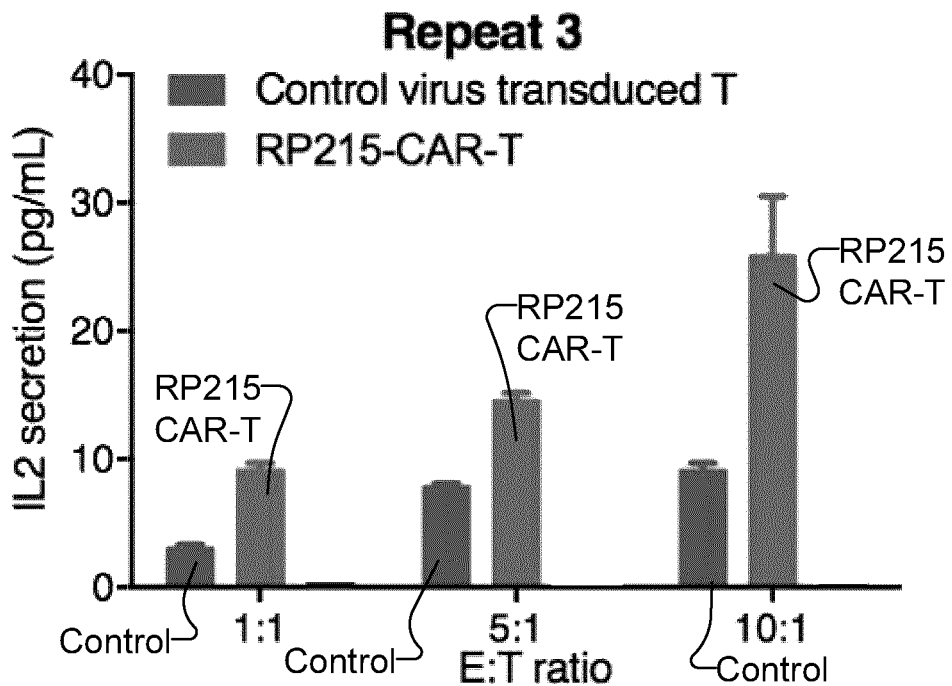
Figure 10E:
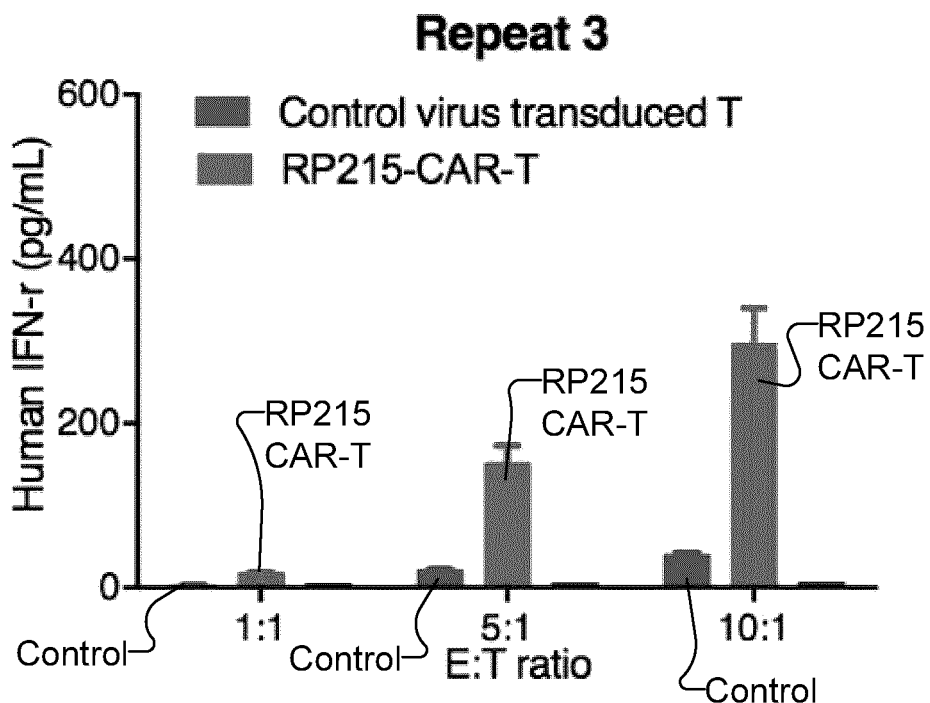
Figure 10F:
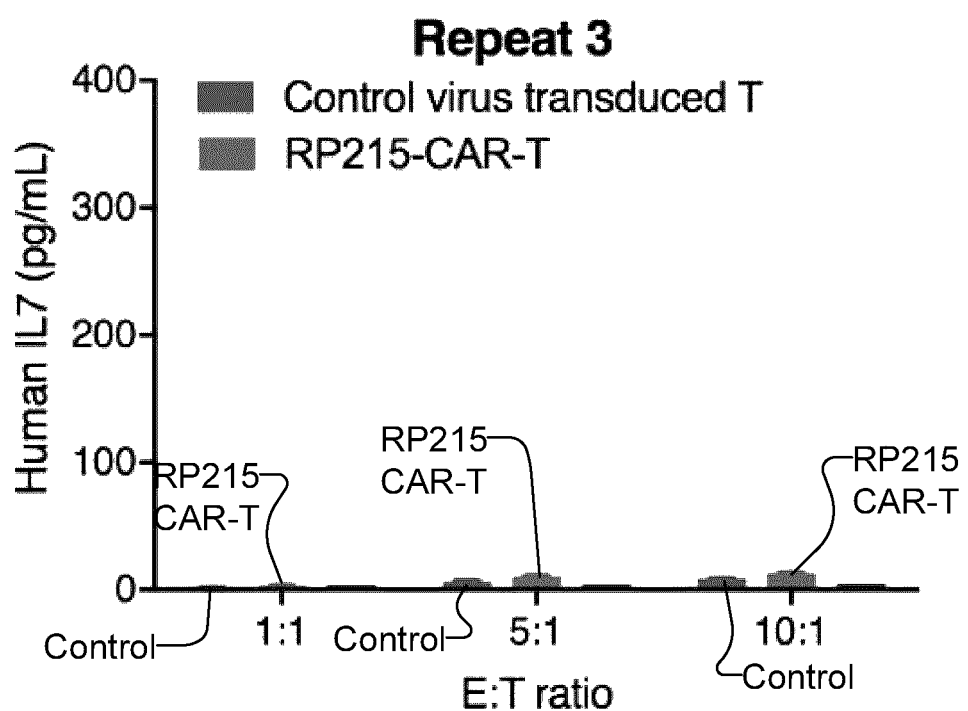

The experiments were repeated three times as shown in FIGS. 7A-7C for comparison.

The results of the lysis assay strongly demonstrate that RP215 CAR-T cells are capable of killing the target tumor cells in a dose dependent manner. The untransduced T cells also showed a low degree of cytolytic effect compared to that of the transduced RP215 CAR cells. Without being bound by theory, this high background could potentially result from the activation of untransfected T cells by anti-CD3 and anti-CD28 antibodies in the assay system tested. The cell lytic effects of RP215 CAR-T cells on the tumor cells are clearly statistically significant ($P$ 0.05-0.001).

Without being bound by theory, the results of this example demonstrate that an RP215 CAR present on the surface of a genetically modified T cell can mediate cytotoxicity toward a target cell. The RP215 binds to CA215 present on a target cell and mediates killing of the target cell by the genetically modified T cell.

Example 7.0: Demonstration of Cytokine Release by CAR-T Cells Upon Co-Culturing with Tumor Cells Using ELISA Assay Upon co-culturing of CAR-T cells with C33A cancer cells for 8 hours, the secretions of different cytokines were determined by typical enzyme immunoassay (EIA). These cytokines including IL-2, IL-7 and IFN-gamma were quantitatively determined and repeated three times.

Briefly, cells are adjusted to logarithmic phase. Adherent cells are lifted with trypsin, and cells are inoculated into assay wells and incubated overnight. RP215 CAR-T cells are harvested by centrifugation and resuspended in 1640 medium without FBS. Target tumor cells are washed with sterilized PBS and RP216 CAR T-cells are added to each well and incubated at 37° C. for 6 hours. Assay plates are centrifuged and supernatant is harvested for detection of IL-2, IL-7 and IFN-gamma using an ELISA assay kit.

Standard curves for three different repeats of the experiment for IL-2, IFN-gamma and IL-7 are shown in FIGS. 8A, 8B, 8C, 9A, 9B, 9C and 10A, 10B, 10C, respectively.

The results of cytokine release enzyme immunoassays for three different repeats assaying IL-2, IFN-gamma and IL-7, respectively, are presented in FIGS. 8D, 8E, 8F, 9D, 9E, 9F and 10D, 10E, 10F for comparison. The cytokine release assay results suggest that significantly more cytokines were released when co-culturing C33A tumor cells with RP215 CAR-T cells than when co-culturing C33A tumor cells with untransfected T cells.

These examples lead to the conclusion that RP215 CAR-T cells (i.e. T cells transduced with a nucleotide vector capable of expressing an RP215 CAR) can effectively lead to cytotoxic killing of co-cultured tumor cells in vitro, and may eventually lead to significant anti-cancer efficacy in vitro or in vivo.

To summarize, the examples discussed above show the following: 1) The results of lentivirus titration showed that the inventor successfully prepared the RP215 CAR lentiviral vectors at a high titer. 2) The qPCR results demonstrate that the lentiviral RP215 CAR vector was transduced into T cells. 3) The lysis assay results demonstrate that RP215 CAR-T cells were able to kill target tumor cells in a "dose-dependent" manner, although untransduced T cells also showed a cytolytic effect, which without being bound by theory may result from the activation of untransduced T cells by anti-CD3 and anti-CD28 antibodies. 4) The cytokine release assay results demonstrate that RP215 CAR-T cells secreted more cytokines than untransduced T cells after co-incubation with target cells.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A nucleotide vector capable of expressing an RP215 CAR, the nucleotide vector encoding a polypeptide having the amino acid sequence of SEQ ID NO:7.

2. An isolated nucleic acid molecule encoding a polypeptide having the amino acid sequence of SEQ ID NO:7.

3. A nucleotide vector as defined in claim 1, wherein the nucleotide vector comprises a lentiviral plasmid suitable for use as a transfer plasmid in a lentiviral vector system to transduce immune cells with a nucleotide sequence capable of expressing RP215 CAR.

4. An RP215 CAR comprising a polypeptide having the amino acid sequence of SEQ ID NO:7.

5. A polypeptide encoded by a nucleotide vector as defined in claim 1, the polypeptide having the amino acid sequence of SEQ ID NO.7.

6. An immune cell comprising a nucleotide vector as defined in claim 1.

* * * * *